(12) United States Patent
Kobayashi et al.

(10) Patent No.: US 10,551,267 B2
(45) Date of Patent: Feb. 4, 2020

(54) DIAPHRAGM TYPE PRESSURE DETECTION DEVICE

(71) Applicant: Surpass Industry Co., Ltd., Gyoda-shi, Saitama (JP)

(72) Inventors: Masamichi Kobayashi, Saitama (JP); Masanori Taguchi, Saitama (JP)

(73) Assignee: SURPASS INDUSTRY CO., LTD, Gyoda-Shi, Saitama (JP)

( * ) Notice: Subject to any disclaimer, the term of this patent is extended or adjusted under 35 U.S.C. 154(b) by 0 days.

(21) Appl. No.: 16/003,383

(22) Filed: Jun. 8, 2018

(65) Prior Publication Data

US 2019/0011321 A1 Jan. 10, 2019

(30) Foreign Application Priority Data

Jul. 5, 2017 (JP) ................................. 2017-132047

(51) Int. Cl.
*G01L 19/00* (2006.01)
*G01L 19/06* (2006.01)
(Continued)

(52) U.S. Cl.
CPC ........ *G01L 19/0023* (2013.01); *G01L 19/003* (2013.01); *A61M 1/3639* (2013.01); *G01L 9/0051* (2013.01); *G01L 19/0627* (2013.01)

(58) Field of Classification Search
CPC ... G01L 19/147; G01L 9/0042; G01L 9/0054; G01L 9/0072; G01L 13/025; G01L 19/04;
(Continued)

(56) References Cited

U.S. PATENT DOCUMENTS 5,036,884 A * 8/1991 Miller ....................... G01F 1/36
137/270
5,292,155 A * 3/1994 Bell .................... G01L 19/0015
285/114
(Continued)

FOREIGN PATENT DOCUMENTS

DE 102007016536 A1 10/2008
JP 2005-207946 A 8/2005

OTHER PUBLICATIONS

European Search Report dated Dec. 5, 2018 in EP Application No. 18176723.7, 13 pages.
(Continued)

*Primary Examiner* — Andre J Allen
(74) *Attorney, Agent, or Firm* — MH2 Technology Law Group, LLP

(57) ABSTRACT

Provided is a pressure detection device which includes: a pressure detection unit configured to detect a pressure transmitted to a diaphragm of the pressure detection unit; a flow passage unit in which a flow passage and a diaphragm of the flow passage unit are formed, a fluid being made to flow through the flow passage along a flow direction from an inflow port to an outflow port, and the diaphragm of the flow passafe unit being configured to transmit a pressure of the fluid flowing through the flow passage to the diaphragm of the flow detection unit; and a nut configured to allow the flow passage unit to be detachably mounted on the pressure detection unit. The pressure detection unit includes a mounting detection sensor configured to detect that the flow passage unit is mounted on the pressure detection unit in a state where the diaphragm of the pressure detection unit and the diaphragm of the flow passage unit are in contact with each other.

8 Claims, 14 Drawing Sheets

(51) Int. Cl.
*G01L 9/00* (2006.01)
*A61M 1/36* (2006.01)

(58) Field of Classification Search
CPC . G01L 19/0038; G01L 19/0084; G01L 19/14;
G01L 9/0075; G01L 19/0069; G01L
19/0618; G01L 9/0055; G01L 9/0073;
G01L 19/0092; G01L 19/0645; G01L
19/143; G01L 9/0051; G01L 9/0052;
G01L 11/025; G01L 19/0007; G01L
19/0046; G01L 19/06; G01L 19/0627;
G01L 19/0681; G01L 27/002; G01L 9/00;
G01L 9/0041; G01L 9/0044; G01L 11/04;
G01L 19/0023; G01L 19/069; G01L
19/142; G01L 19/16; G01L 7/00; G01L
7/163; G01L 7/166; G01L 9/0047; G01L
9/12; G01L 11/02; G01L 13/00; G01L
15/00; G01L 19/003; G01L 19/0609;
G01L 19/0672; G01L 19/083; G01L
19/10; G01L 19/148; G01L 27/005; G01L
7/08; G01L 7/082; G01L 9/0045; G01L
9/0048; G01L 9/006; G01L 9/007; G01L
9/0076; G01L 9/04; G01L 9/045; G01L
9/06; G01L 9/065; G01L 9/125; G01L
11/00; G01L 17/00; G01L 19/00; G01L
19/0015; G01L 19/0076; G01L 19/02;
G01L 19/08; G01L 19/141; G01L 19/145;
G01L 19/146; G01L 1/142; G01L 1/2262;
G01L 1/246; G01L 21/12; G01L 23/16;
G01L 27/007; G01L 7/04; G01L 7/063;
G01L 7/084; G01L 7/086; G01L 7/16;
G01L 9/0002; G01L 9/0007; G01L
9/0016; G01L 9/0019; G01L 9/0022;
G01L 9/0027; G01L 9/0033; G01L
9/0039; G01L 9/005; G01L 9/0058; G01L
9/0077; G01L 9/0079; G01L 9/008; G01L
9/0092; G01L 9/0095; G01L 9/025; G01L
9/08; G01L 9/085; G01L 9/105; G01L
9/14; G01L 9/16
USPC .................................................. 73/700–756
See application file for complete search history.

(56) References Cited

U.S. PATENT DOCUMENTS

| | | |
|---|---|---|
| 5,693,008 A | 12/1997 | Bruggar et al. |
| 2005/0160828 A1 | 7/2005 | Hasunuma |
| 2011/0011176 A1 | 1/2011 | Glocker |
| 2011/0041619 A1 | 2/2011 | Delbos et al. |
| 2013/0003780 A1 | 1/2013 | Delbos et al. |
| 2013/0205907 A1* | 8/2013 | Fukano .................. G01L 7/08 73/715 |
| 2014/0076058 A1 | 3/2014 | Bruggar et al. |
| 2015/0137281 A1* | 5/2015 | Imai .................. B81B 7/0051 257/415 |
| 2016/0305798 A1* | 10/2016 | Breunig ................ G01L 19/003 |
| 2016/0377499 A1* | 12/2016 | Imai .................. G01L 19/147 73/756 |
| 2017/0028119 A1 | 2/2017 | Bruggar et al. |
| 2018/0128698 A1 | 5/2018 | Bruggar et al. |
| 2018/0238761 A1* | 8/2018 | Imai .................. G01L 19/0023 |
| 2019/0056280 A1* | 2/2019 | Abo .................. G01L 9/0051 |

OTHER PUBLICATIONS

Extended European Search Report dated Apr. 24, 2019 in EP Application No. 18176723.7, 13 pages.

* cited by examiner

DIAPHRAGM TYPE PRESSURE DETECTION DEVICE

CROSS-REFERENCE TO RELATED APPLICATIONS

This application is based on Japanese Patent Application No. 2017-132047, the contents of which are incorporated herein by reference in its entirety.

TECHNICAL FIELD

The present disclosure relates to a pressure detection device provided with a mounting mechanism which allows a flow passage unit to be detachably mounted on a pressure detection unit.

BACKGROUND

An inline pressure sensor can include a body and a sensor body formed into one integral body, wherein a flow passage, through which a liquid such as a liquid medicine is made to flow, is formed in the body, and the sensor body detects a pressure of the liquid which is transmitted to a pressure receiving surface through a protective sheet. See Japanese Unexamined Patent Application, Publication No. 2005-207946, for example.

The pressure sensor disclosed in the above-referenced unexamined application is configured such that a sensor body is fixed to the body by a sensor holder in a state where the sensor body is mounted on an upper surface of the body, and a body cap is mounted on the upper surface of the body thus forming these members into an integral body.

SUMMARY

The following presents a simplified summary in order to provide a basic understanding of some aspects of one or more implementations of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

In an implementation, a pressure detection device can include a pressure detection unit configured to detect a pressure transmitted to a pressure detection surface, a flow passage unit in which a flow passage and a pressure transmitting surface are formed, a fluid being made to flow through the flow passage along a flow direction from an inflow port to an outflow port, the pressure transmitting surface being configured to transmit a pressure of the fluid flowing through the flow passage to the pressure detection surface, and a mounting mechanism configured to allow the flow passage unit to be detachably mounted on the pressure detection unit. The pressure detection unit can include a detection part configured to detect that the flow passage unit is mounted on the pressure detection unit in a state where the pressure detection surface and the pressure transmitting surface are in contact with each other.

The pressure detection unit can include a pair of guide parts having groove portions configured to guide a portion of the flow passage on an inflow port side and a portion of the flow passage on an outflow port side to a predetermined mounting position in mounting the flow passage unit on the pressure detection unit, and the detection part is disposed on at least either one of the pair of guide parts, and the detection part detects that the flow passage unit is mounted on the pressure detection unit with the detection of the flow passage guided to the predetermined mounting position.

The the pressure detection unit can further include a setting part configured to set a pressure detected by the pressure detection surface as a reference value corresponding to a predetermined instruction, and the setting part sets the reference value corresponding to the predetermined instruction in a state where the detection part detects that the flow passage unit is mounted on the pressure detection unit.

The pressure detection unit can further include a first positioning portion extending in a first axial direction extending along a first axis orthogonal to the pressure detection surface, and the flow passage unit can include a second positioning portion extending in a second axial direction extending along a second axis orthogonal to the pressure transmitting surface. The mounting mechanism can allow the flow passage unit to be mounted on the pressure detection unit in a state where the first axis and the second axis agree with each other, and a position of the first positioning portion about the first axis and a position of the second positioning portion about the second axis agree with each other.

The pressure detection unit can include a projecting portion where the pressure detection surface is disposed at a top portion of the projecting portion, and the first positioning portion is formed on an outer peripheral surface of the projecting portion. The flow passage unit can have a recessed portion where the pressure transmitting surface is disposed at a bottom portion of the recessed portion, and the second positioning portion can be formed on an inner peripheral surface of the recessed portion. The mounting mechanism can allow the flow passage unit to be mounted on the pressure detection unit in a state where the projecting portion of the pressure detection unit is inserted into the recessed portion of the flow passage unit.

The first positioning portion can be formed of a plurality of protrusions formed on the outer peripheral surface of the projecting portion, the second positioning portion can be formed of a plurality of grooves formed on the inner peripheral surface of the recessed portion, and the mounting mechanism can allow the flow passage unit to be mounted on the pressure detection unit in a state where the first axis and the second axis agree with each other, and respective positions of the plurality of protrusions about the first axis and respective positions of the plurality of grooves about the second axis agree with each other.

The mounting mechanism can be formed of a nut mounted on the flow passage unit in a rotatable manner about the second axis, a female thread being formed on an inner peripheral surface of the nut. A male thread can be formed on an outer peripheral surface of the pressure detection unit disposed more outward than the projecting portion. The pressure transmitting surface can come into contact with the pressure detection surface by fastening the female thread formed on the nut to the male thread. Further, a distal end of the female thread in a direction of the first axis and a distal end of the male thread in a direction of the second axis can come into contact with each other in a state where a portion of the first positioning portion in the direction of the first axis and a portion of the second positioning portion in the direction of the second axis are engaged with each other.

DETAILED DESCRIPTION

Figure 1:
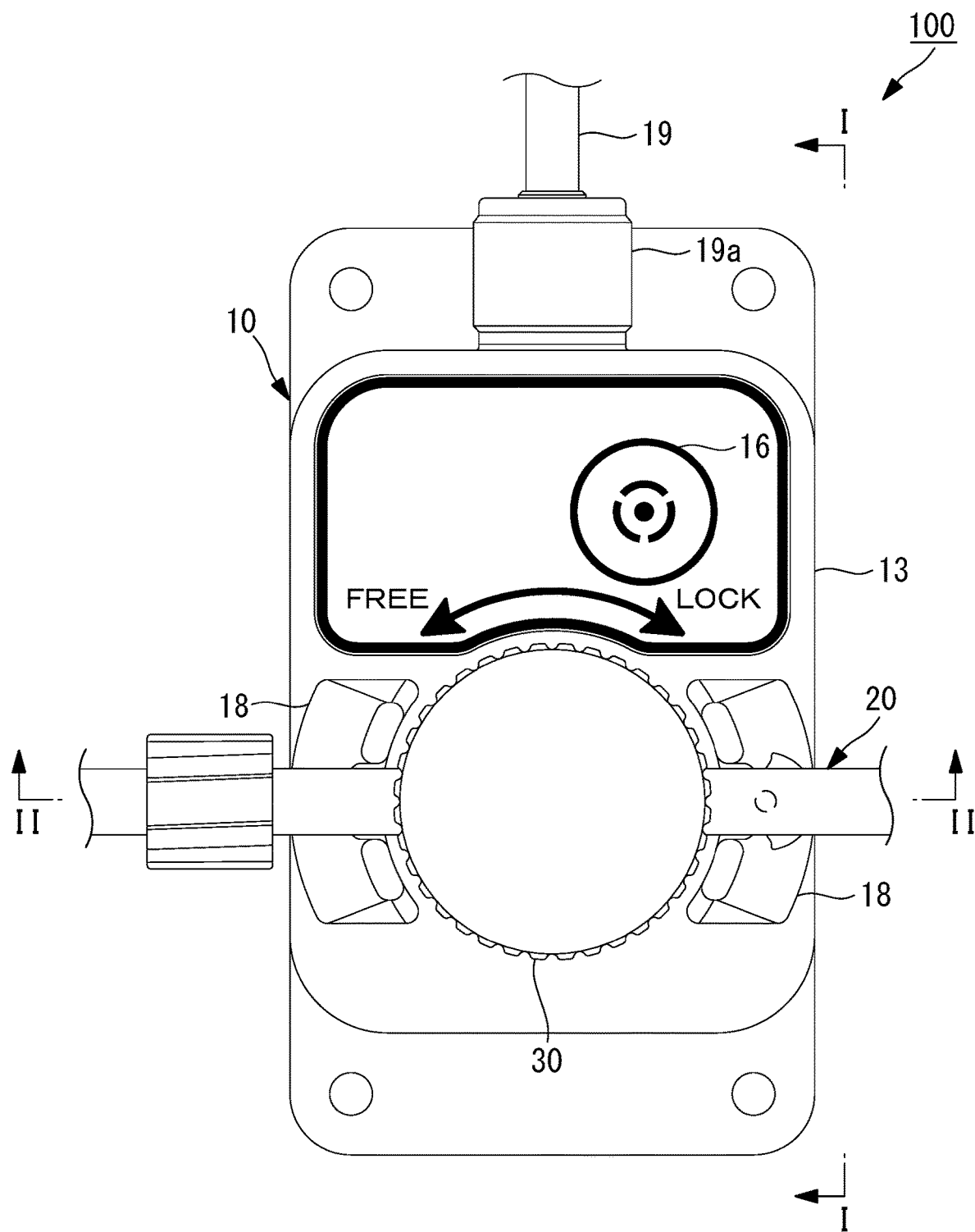
FIG. 1 is a front view showing a pressure detection device of a first embodiment.

In the pressure sensor disclosed in Patent Literature 1, the body, in which the flow passage is formed, and the sensor body are formed into one integral body. Accordingly, in changing a liquid forming a detection target, it is necessary to wash the existing flow passage with pure water or the like. However, it is difficult to completely remove a liquid remaining in the flow passage with the method of washing the flow passage and, at the same time, such a method requires a lot of time for performing a washing operation. Accordingly, for example, in a medical field or the like which requires a flow passage where the inside of the flow passage is sterilized or the like thus being completely clean, the method of washing the flow passage in changing a liquid is not sufficient in view of smoothness and safety of the operation.

The present disclosure has been made under such circumstances, and it is an object of the present disclosure to provide a pressure detection device which can improve smoothness and safety of the operation of changing a fluid which is made to flow through a flow passage, and can also reliably detect that the pressure detection device is in a state which can normally detect a pressure of a fluid.

To solve the above-mentioned problem, the present disclosure adopts the following solutions.

A pressure detection device according to one aspect of the present disclosure includes: a pressure detection unit configured to detect a pressure transmitted to a pressure detection surface; a flow passage unit in which a flow passage and a pressure transmitting surface are formed, a fluid being made to flow through the flow passage along a flow direction from an inflow port to an outflow port, the pressure transmitting surface being configured to transmit a pressure of the fluid flowing through the flow passage to the pressure detection surface; and a mounting mechanism configured to allow the flow passage unit to be detachably mounted on the pressure detection unit, wherein the pressure detection unit includes a detection part configured to detect that the flow passage unit is mounted on the pressure detection unit in a state where the pressure detection surface and the pressure transmitting surface are in contact with each other.

According to the pressure detection device of one aspect of the present disclosure, the flow passage unit is detachably mounted on the pressure detection unit. Accordingly, to change a fluid which is made to flow through the flow passage, the flow passage unit which is already used is removed from the pressure detection unit, and a flow passage unit which is unused can be newly mounted on the pressure detection unit.

With such a configuration, in changing a fluid to be made to flow through the flow passage, it becomes unnecessary to perform a washing operation of the flow passage, which requires a lot of time, so that smoothness of the operation can be improved. Further, a flow passage unit which is unused can be newly used and hence, safety can be improved.

According to the pressure detection device of one aspect of the present disclosure, the detection part can detect that the flow passage unit is mounted on the pressure detection unit in a state where the pressure detection surface and the pressure transmitting surface are in contact with each other. Accordingly, it is possible to prevent a problem of the flow passage unit being mounted on the pressure detection unit in a state where the pressure detection surface and the pressure transmitting surface are not in contact with each other so that a pressure of a fluid cannot be normally detected.

As described above, according to the pressure detection device of one aspect of the present disclosure, it is possible to improve smoothness and safety of the operation of changing a fluid which is made to flow through the flow passage, and it is also possible to reliably detect that the pressure detection device is in a state which can normally detect a pressure of a fluid.

In the pressure detection device according to one aspect of the present disclosure, the pressure detection unit may include a pair of guide parts having groove portions configured to guide a portion of the flow passage on an inflow port side and a portion of the flow passage on an outflow port side to a predetermined mounting position in mounting the flow passage unit on the pressure detection unit, and the detection part may be disposed on at least either one of the pair of guide parts, and the detection part may detect that the flow passage unit is mounted on the pressure detection unit with the detection of the flow passage guided to the predetermined mounting position.

According to the pressure detection device having this configuration, in mounting the flow passage unit on the pressure detection unit, the portion of the flow passage on the inflow port side and the portion of the flow passage on the outflow port side are guided to the predetermined mounting position by the pair of guide parts. Accordingly, the flow passage unit can be reliably mounted on the predetermined mounting position. Further, the detection part can reliably detect that the flow passage unit is mounted normally on the pressure detection unit with the detection of the flow passage guided to the predetermined mounting position.

In the pressure detection device according to one aspect of the present disclosure, the pressure detection unit may include a setting part configured to set a pressure detected by the pressure detection surface as a reference value corresponding to a predetermined instruction, and the setting part may set the reference value corresponding to the predetermined instruction in a state where the detection part detects that the flow passage unit is mounted on the pressure detection unit.

According to the pressure detection device having this configuration, a reference value is set in a state where the detection part detects that the flow passage unit is mounted on the pressure detection unit. Accordingly, it is possible to prevent a problem of an incorrect pressure being erroneously set as a reference value in a state where the detection part does not detect that the flow passage unit is mounted on the pressure detection unit.

In the pressure detection device according to one aspect of the present disclosure, the pressure detection unit may include a first positioning portion extending in a first axial direction extending along a first axis orthogonal to the pressure detection surface, the flow passage unit may include a second positioning portion extending in a second axial direction extending along a second axis orthogonal to the pressure transmitting surface, and the mounting mechanism may allow the flow passage unit to be mounted on the pressure detection unit in a state where the first axis and the second axis agree with each other, and a position of the first positioning portion about the first axis and a position of the second positioning portion about the second axis agree with each other.

According to the pressure detection device having this configuration, the mounting mechanism allows the flow passage unit to be mounted on the pressure detection unit in a state where the first axis and the second axis agree with each other, and the position of the first positioning portion of the pressure detection unit about the first axis and the position of the second positioning portion of the flow passage unit about the second axis agree with each other. Accordingly, the direction that the flow passage unit is disposed about the second axis assumes a predetermined direction with respect to the direction that the pressure detection unit is disposed about the first axis.

With such a configuration, the positions of the inflow port and the outflow port of the flow passage formed in the flow passage unit assume predetermined positions with respect to the pressure detection unit so that connectivity of a pipe to be connected to the inflow port and connectivity of a pipe to be connected to the outflow port can be enhanced.

In the pressure detection device according to one aspect of the present disclosure, the pressure detection unit may have a projecting portion where the pressure detection surface is disposed at a top portion of the projecting portion, and the first positioning portion is formed on an outer peripheral surface of the projecting portion, the flow passage unit may have a recessed portion where the pressure transmitting surface is disposed at a bottom portion of the recessed portion, and the second positioning portion is formed on an inner peripheral surface of the recessed portion, and the mounting mechanism may allow the flow passage unit to be mounted on the pressure detection unit in a state where the projecting portion of the pressure detection unit is inserted into the recessed portion of the flow passage unit.

With such a configuration, the pressure transmitting surface is disposed at the bottom portion of the recessed portion of the flow passage unit. Accordingly, in exchanging the flow passage unit, it is possible to suppress a problem of an operator inadvertently coming into contact with the pressure transmitting surface and a problem of the pressure transmitting surface coming into contact with other members thus being damaged.

In the pressure detection device having the above-mentioned configuration, the first positioning portion may be formed of a plurality of protrusions formed on the outer peripheral surface of the projecting portion, the second positioning portion may be formed of a plurality of grooves formed on the inner peripheral surface of the recessed portion, and the mounting mechanism may allow the flow passage unit to be mounted on the pressure detection unit in a state where the first axis and the second axis agree with each other, and respective positions of the plurality of protrusions about the first axis and respective positions of the plurality of grooves about the second axis agree with each other.

With such a configuration, it is possible to prevent that the flow passage unit is mounted on the pressure detection unit in a state where the respective positions of the plurality of protrusions, formed on the outer peripheral surface of the projecting portion of the pressure detection unit, about the first axis and the respective positions of the plurality of grooves, formed on the inner peripheral surface of the recessed portion of the flow passage unit, about the second axis do not agree with each other. Accordingly, it is possible to suppress a problem of the flow passage unit being mounted on the pressure detection unit in a state where the flow passage of the flow passage unit does not agree with a desired mounting position.

In the pressure detection device according to one aspect of the present disclosure, the mounting mechanism may be formed of a nut mounted on the flow passage unit in a rotatable manner about the second axis, a female thread being formed on an inner peripheral surface of the nut, a male thread may be formed on an outer peripheral surface of the pressure detection unit disposed more outward than the projecting portion, and the pressure transmitting surface may come into contact with the pressure detection surface by fastening the female thread formed on the nut to the male thread.

With such a configuration, the pressure detection surface of the pressure detection unit and the pressure transmitting surface of the flow passage unit gradually approach each other when an operator rotates the nut mounted on the flow passage unit about the second axis, and, eventually, the pressure detection surface and the pressure transmitting surface come into contact with each other. With a relatively simple operation of rotating the mounting mechanism about the second axis, a distance between the pressure detection surface and the pressure transmitting surface is gradually reduced and, then, the pressure detection surface and the pressure transmitting surface can be reliably brought into contact with each other. Accordingly, the pressure detection surface and the pressure transmitting surface can be relatively easily brought into contact with each other without causing a problem of the pressure detection surface and the pressure transmitting surface being forcefully brought into contact with each other and thus being damaged.

In the pressure detection device having the above-mentioned configuration, a distal end of the female thread in a direction of the first axis and a distal end of the male thread in a direction of the second axis may come into contact with each other in a state where a portion of the first positioning portion in the direction of the first axis and a portion of the second positioning portion in the direction of the second axis are engaged with each other.

With such a configuration, after a direction that the flow passage unit is disposed about the second axis assumes a predetermined direction with respect to a direction that the pressure detection unit is disposed about the first axis, the nut is rotated about the first axis thus allowing the flow passage unit to be mounted on the pressure detection unit. Accordingly, compared to a case where the engagement between the first positioning portion and the second positioning portion is started simultaneously with or after the fastening of the nut to the flow passage unit, the flow passage unit can be easily mounted on the pressure detection unit.

According to the present disclosure, it is possible to provide a pressure detection device which can improve smoothness and safety of the operation of changing a fluid which is made to flow through the flow passage, and also can reliably detect that the pressure detection device is in a state which can normally detect a pressure of a fluid.

First Embodiment

Hereinafter, a pressure detection device 100 according to a first embodiment of the present disclosure is described with reference to drawings.

Figure 2:
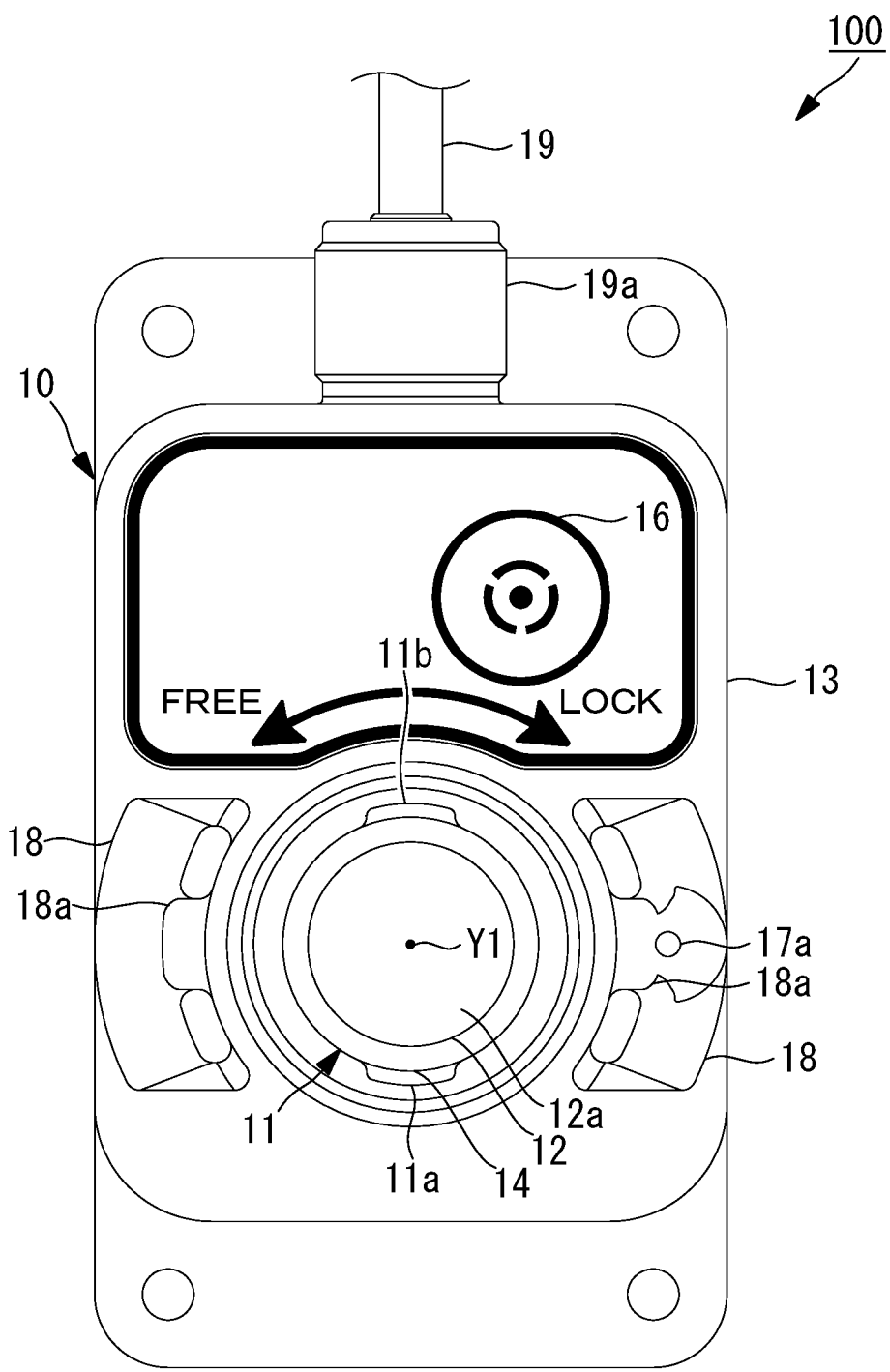
FIG. 2 is a view showing a state where a flow passage unit is removed from the pressure detection device shown in FIG. 1.

As shown in FIG. 1 and FIG. 2, the pressure detection device 100 of this embodiment includes: a pressure detection unit 10; a flow passage unit 20; and a nut (mounting mechanism) 30. The pressure detection unit 10 is mounted on an installation surface S (see FIG. 3) by fastening bolts (not shown in the drawing). A flow passage 21 is formed in the flow passage unit 20, and a fluid is made to flow through the flow passage 21 along a straight-line flow direction from an inflow port 21a to an outflow port 21b. The nut (mounting mechanism) 30 allows the flow passage unit 20 to be detachably mounted on the pressure detection unit 10.

In the pressure detection device 100 of this embodiment, the flow passage unit 20 is mounted on the pressure detection unit 10 by the nut 30. The pressure detection device 100 is mounted on the installation surface S in a state where the flow passage unit 20 is mounted on the pressure detection unit 10 by the nut 30 thus forming an integral body.

Figure 3:
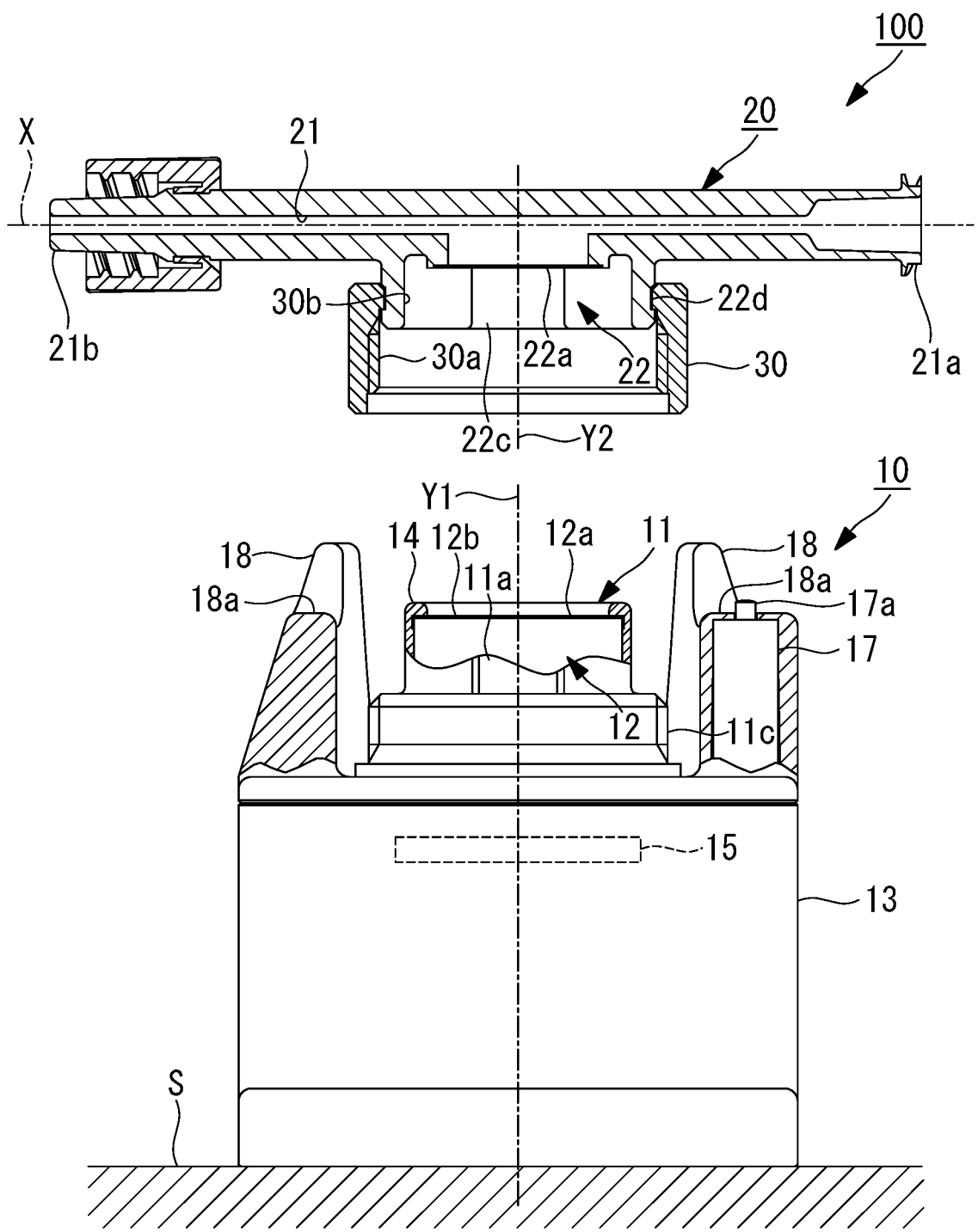
FIG. 3 is a cross-sectional view showing a state where the flow passage unit is removed from the pressure detection device shown in FIG. 1 as viewed from an arrow I-I.
Figure 4:
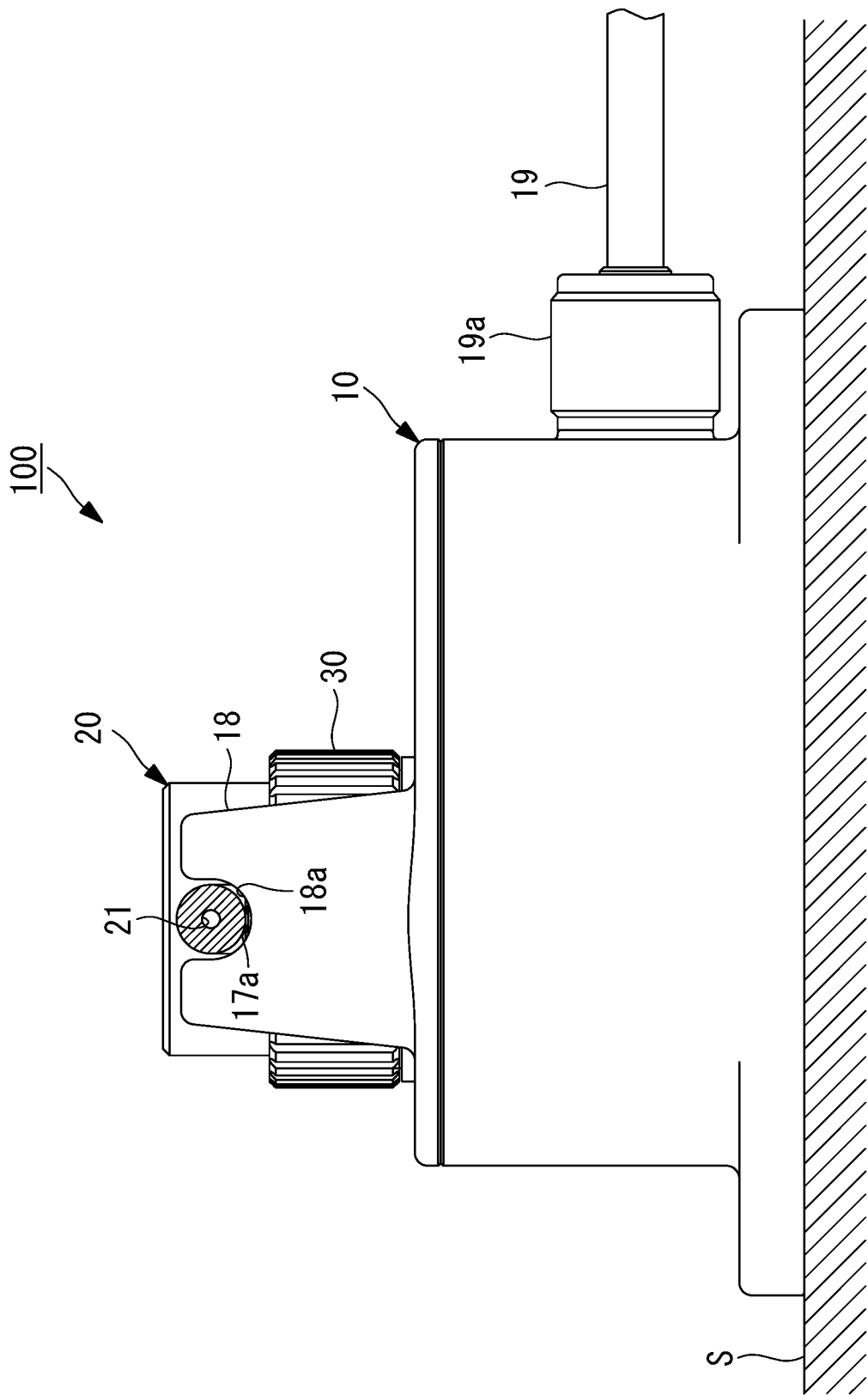
FIG. 4 is a view of the pressure detection device shown in FIG. 1 as viewed from an arrow I-I.

As shown in FIG. 3 and FIG. 4, an inflow side pipe (not shown in the drawing), through which a fluid is made to flow in the inflow port 21a, is mounted on the inflow port 21a of the flow passage unit 20. An outflow side pipe (not shown in the drawing), through which the fluid flowing out from the outflow port 21b flows, is mounted on the outflow port 21b of the flow passage unit 20. A pressure of a fluid flowing through the flow passage 21 from the inflow port 21a to the outflow port 21b is detected by the pressure detection unit 10.

In this embodiment, a fluid means a liquid such as blood or a dialysate, for example.

As shown in FIG. 3, the pressure detection unit 10 includes a body portion 13 mounted on the installation surface S. As shown in FIG. 2 and FIG. 3, a cable 19 is mounted on the body portion 13 of the pressure detection unit 10 by way of a cable mounting nut 19a. The cable 19 electrically connects a pressure sensor 12, which is disposed in the body portion 13, and a control device (not shown in the drawing) disposed outside the body portion 13 with each other.

Next, the pressure detection unit 10 is described in detail with reference to FIG. 1 to FIG. 3. The pressure detection unit 10 shown in FIG. 1 to FIG. 3 is a device which detects a pressure transmitted to a diaphragm 12a.

As shown in FIG. 1 to FIG. 3, the pressure detection unit 10 includes: the body portion 13; the pressure sensor 12 disposed in the body portion 13; a sensor holding portion 14 which holds the pressure sensor 12 onto the body portion 13; a sensor board (setting part) 15 for transmitting power and an electric signal between the pressure sensor 12 and the cable 19; a zero-point adjustment switch 16 for performing a zero-point adjustment of the pressure sensor 12; a mounting detection sensor (detection part) 17 which detects that the flow passage unit 20 is mounted on the pressure detection unit 10; and a pair of guide members (guide parts) 18 which guides the flow passage 21 of the flow passage unit 20 to a predetermined mounting position.

As shown in FIG. 3, the pressure sensor 12 includes: the diaphragm (pressure detection surface) 12a formed into a thin film shape using a material having corrosion resistance (for example, sapphire); a strain resistance (not shown in the drawing) adhered to the diaphragm 12a; and a base portion 12b which holds the diaphragm 12a.

The pressure sensor 12 is a strain type sensor. The strain type sensor outputs a pressure signal which corresponds to a change in strain resistance, which deforms together with the diaphragm 12a corresponding to a pressure transmitted to the strain resistance. A through hole (not shown in the drawing), which communicates with the diaphragm 12a, is formed in the base portion 12b so that one surface of the diaphragm 12a is maintained at an atmospheric pressure. Accordingly, the pressure sensor 12 is a sensor which detects a gauge pressure using an atmospheric pressure as a reference.

The sensor holding portion 14 is a member formed into a cylindrical shape about an axis (first axis) Y1. Positioning protrusions (first positioning portions) 11a, 11b are formed on an outer peripheral surface of the sensor holding portion 14. An inner diameter of an upper end of the sensor holding portion 14 is smaller than an outer diameter of the pressure sensor 12 so that the sensor holding portion 14 can hold the pressure sensor 12 while preventing the pressure sensor 12 from removing in the upward direction.

The sensor board 15 includes: an amplifier circuit (not shown in the drawing) which amplifies a pressure signal outputted from the pressure sensor 12; an interface circuit which transmits the pressure signal, amplified by the amplifier circuit, to a pressure signal line (not shown in the drawing) of the cable 19; a power supply circuit (not shown in the drawing) which transmits a power supply voltage supplied from the outside through the cable 19 to the pressure sensor 12; a zero-point adjustment circuit (not shown in the drawing) which performs a zero-point adjustment when the zero-point adjustment switch 16 is pressed and the like.

The zero-point adjustment circuit is a circuit which performs an adjustment such that, when the zero-point adjustment switch 16 is pressed, a pressure signal outputted from the pressure sensor 12 at that point of time is set as a reference value (for example, zero).

As shown in FIG. 3, the pressure sensor 12 and the sensor holding portion 14 of the pressure detection unit 10 form a projecting portion 11 which projects upward from the body portion 13 along the axis Y1 and where the diaphragm 12a is disposed at a top portion of the projecting portion 11. The positioning protrusions 11a, 11b, which extend in the axial direction extending along the axis Y1, are formed on an outer peripheral surface of the projecting portion 11.

As shown in FIG. 2 and FIG. 3, the diaphragm 12a is disposed on a plane orthogonal to the axis Y1. Accordingly, the positioning protrusions 11a, 11b are formed on the outer peripheral surface of the projecting portion 11 so as to extend in the axial direction extending along the axis Y1 orthogonal to the diaphragm 12a.

FIG. 2 is a view showing a state where the flow passage unit 20 is removed from the pressure detection device 100 shown in FIG. 1. As shown in FIG. 2, the positioning protrusions 11a, 11b are formed on the outer peripheral surface of the projecting portion 11, and are formed at two positions at intervals of 180° about the axis Y1. As shown in FIG. 2, in a state where the flow passage unit 20 is not mounted on the pressure detection unit 10, the diaphragm 12a of the pressure sensor 12 is exposed to the outside.

The mounting detection sensor 17 is a sensor which detects that the flow passage unit 20 is mounted on the pressure detection unit 10. As shown in FIG. 2 and FIG. 3, a detecting protrusion 17a is provided to an upper end of the mounting detection sensor 17, and the detecting protrusion 17a is biased upward in the vertical direction by a biasing member (not shown in the drawing) such as a spring. The mounting detection sensor 17 is disposed in a state where portions of the mounting detection sensor 17 excluding the detecting protrusion 17a are accommodated in the guide member 18 described later.

The guide members 18 are members each of which has a groove portion 18a for guiding the flow passage 21 to a predetermined mounting position in mounting the flow passage unit 20 on the pressure detection unit 10. The pairs of guide members 18 are provided at positions which are symmetrical with respect to the axis Y1. The pair of guide members 18 respectively guide a portion of the flow passage 21 on the inflow port 21a side and a portion of the flow passage 21 on the outflow port 21b side to predetermined mounting positions. The predetermined mounting position means a position which causes a state where, as shown in FIG. 4, an outer peripheral surface of the flow passage 21 is surrounded by the groove portion 18a of the guide member 18, and a lower end of the flow passage 21 presses the detecting protrusion 17a of the mounting detection sensor 17 in the downward direction.

Next, the flow passage unit 20 is described in detail with reference to FIG. 3 and FIG. 5 to FIG. 8.

As shown in FIG. 5 to FIG. 8, the flow passage unit 20 has the flow passage 21 and a recessed portion 22. The flow passage 21 extends from the inflow port 21a to the outflow port 21b along an axis X, and a fluid is made to flow through the flow passage 21 in the flow direction. A diaphragm (pressure transmitting surface) 22a is disposed at a bottom portion of the recessed portion 22, and positioning grooves (second positioning portions) 22b, 22c are formed on an inner peripheral surface of the recessed portion 22.

Figure 5:
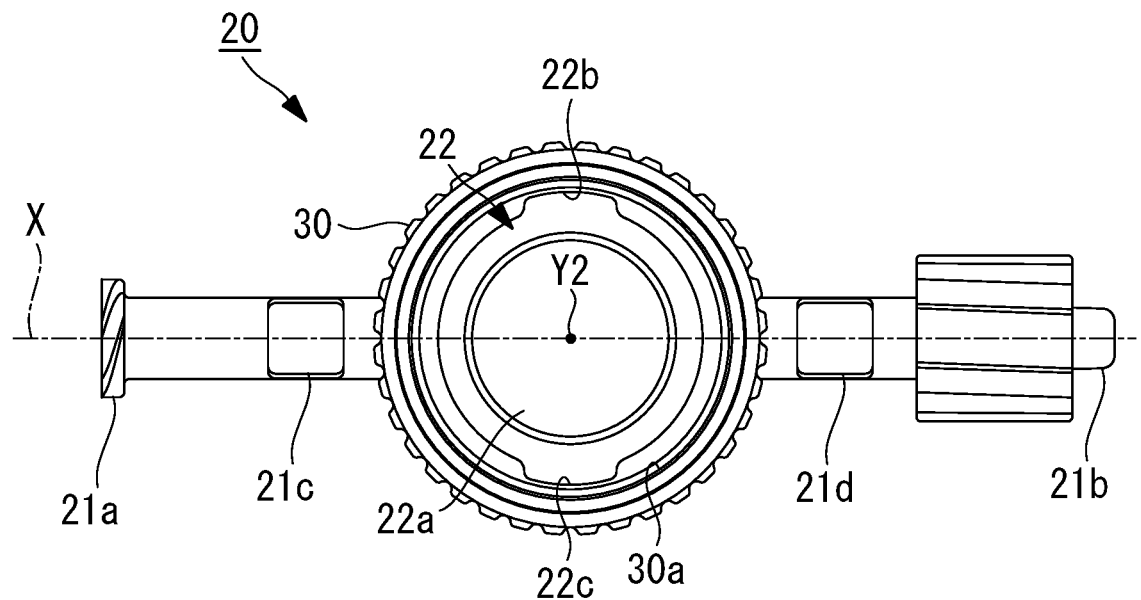
FIG. 5 is a back view of the flow passage unit shown in FIG. 1.
Figure 7:
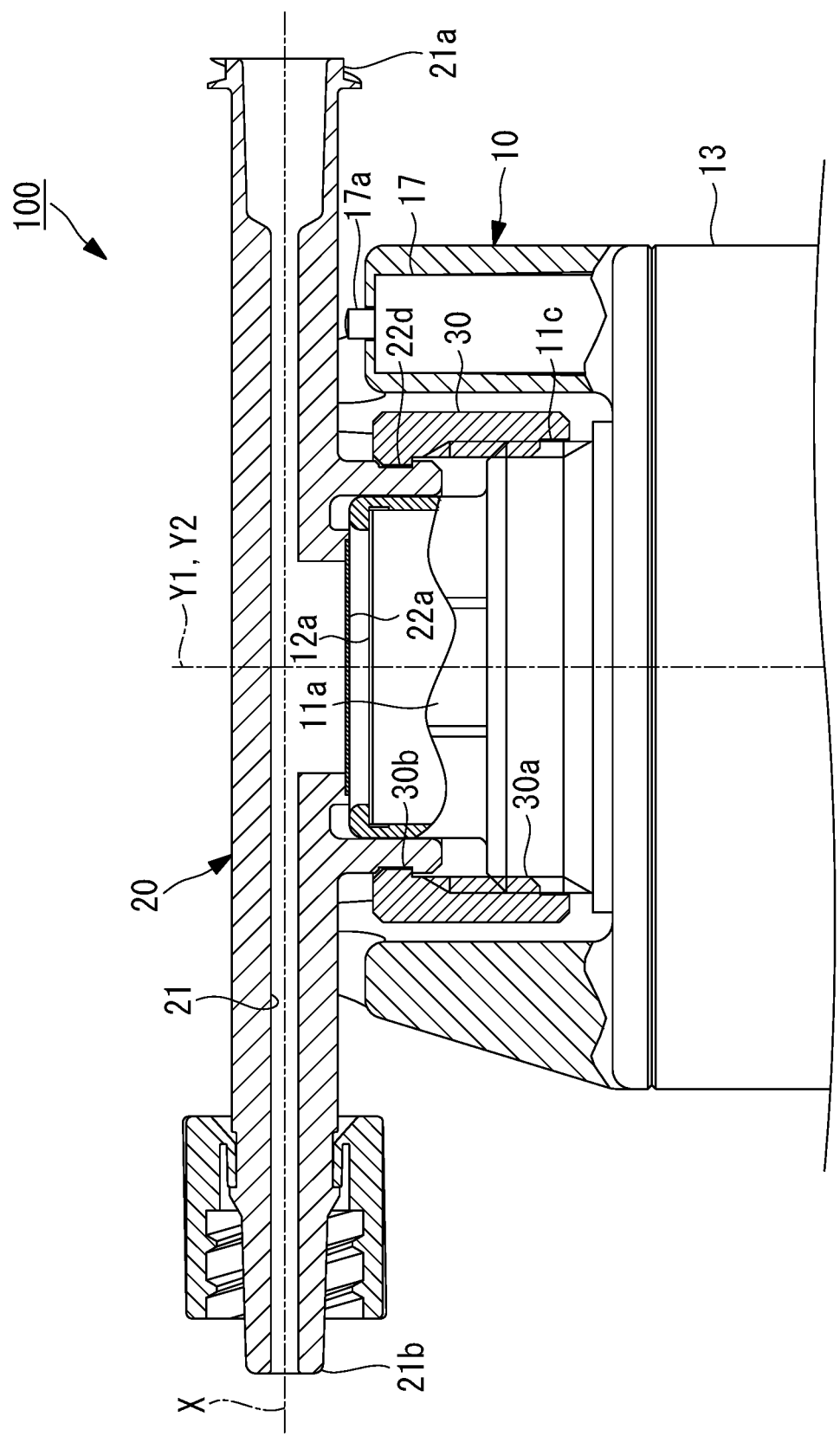
FIG. 7 is a cross-sectional view of the pressure detection device shown in FIG. 1 as viewed from an arrow II-II showing a state in the course of mounting the flow passage unit on a pressure detection unit.
Figure 8:
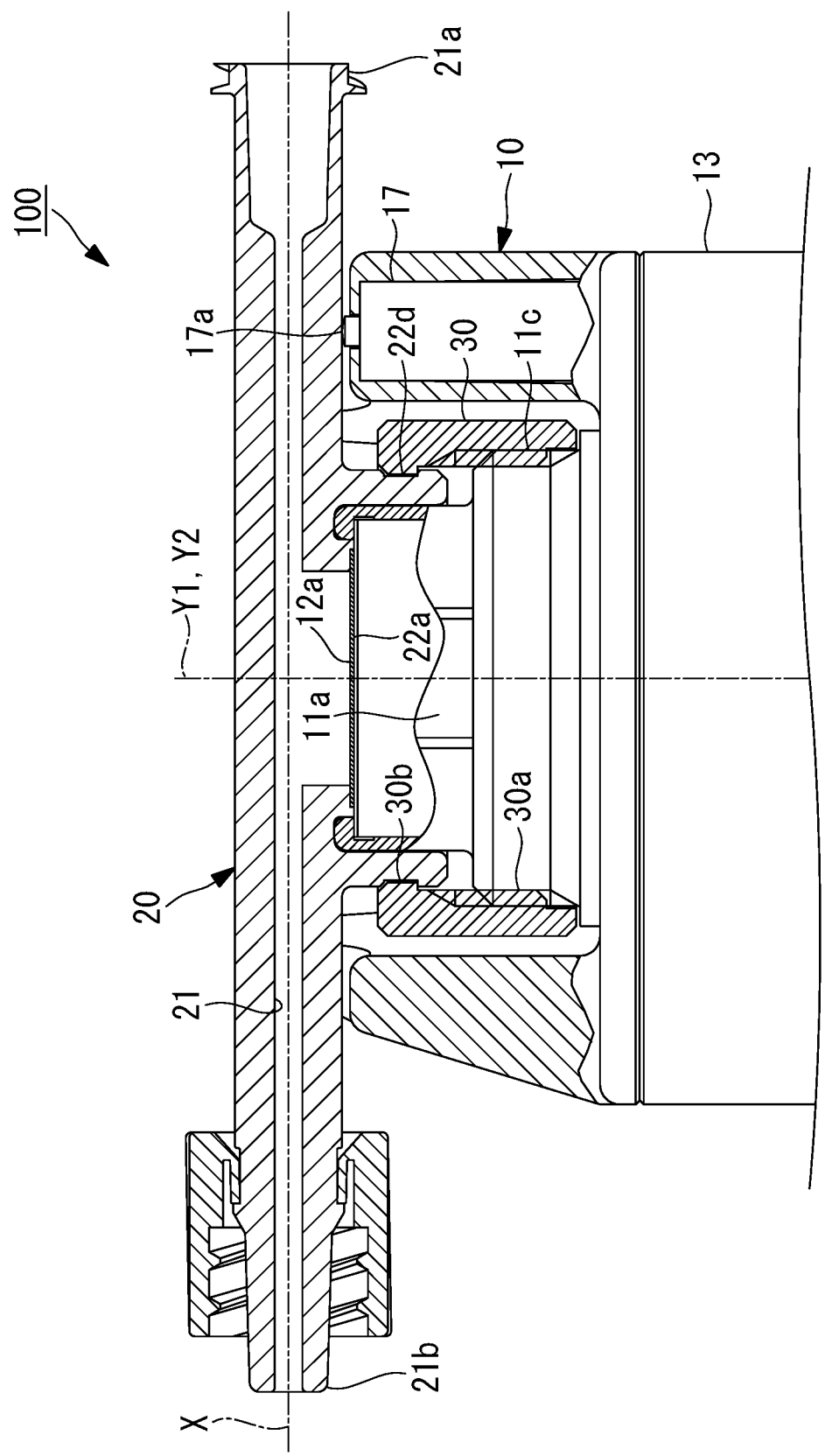
FIG. 8 is a cross-sectional view of the pressure detection device shown in FIG. 1 as viewed from an arrow II-II showing a state where the flow passage unit is mounted on the pressure detection unit.

As shown in FIG. 5, FIG. 7, and FIG. 8, the diaphragm 22a is disposed on a horizontal plane orthogonal to an axis (second axis) Y2. Accordingly, the positioning grooves 22b, 22c are formed on the inner peripheral surface of the recessed portion 22 so as to extend in the axial direction extending along the axis Y2 orthogonal to the diaphragm 22a.

The diaphragm 22a is a member formed into a thin film shape using a material having corrosion resistance (for example, silicone resin material). The diaphragm 22a is a member formed into a circular shape as viewed in a plan view with the axis Y2 as a center axis. An outer peripheral edge portion of the diaphragm 22a is mounted on the bottom portion of the recessed portion 22 by bonding or by welding. Accordingly, there is no possibility that a fluid introduced into the flow passage 21 flows out to the outside from the flow passage 21. The diaphragm 22a is formed into a thin film shape so that the diaphragm 22a is deformed due to a pressure of a fluid introduced into the flow passage 21.

In a state shown in FIG. 7 where the flow passage unit 20 is in the course of being mounted on the pressure detection unit 10, the diaphragm 22a of the flow passage unit 20 is separated at a distance from the diaphragm 12a of the pressure detection unit 10. On the other hand, in a state shown in FIG. 8 where the flow passage unit 20 is mounted on the pressure detection unit 10, the diaphragm 22a of the flow passage unit 20 is in contact with the diaphragm 12a of the pressure detection unit 10. Accordingly, the diaphragm 22a forms a pressure transmitting surface for transmitting a pressure of a fluid which flows through the flow passage 21 to the diaphragm 12a.

FIG. 5 is a back view of the flow passage unit 20 shown in FIG. 1. As shown in FIG. 5, the positioning grooves 22b, 22c are formed on the inner peripheral surface of the recessed portion 22, and are formed at two positions at intervals of 180° about the axis Y2. As shown in FIG. 5, in a state where the flow passage unit 20 is not mounted on the pressure detection unit 10, the diaphragm 22a is exposed to the outside. However, the diaphragm 22a is disposed on the bottom portion of the recessed portion 22 and hence, there is a low risk of an operator inadvertently coming into contact with the diaphragm 22a.

As shown in FIG. 3, an endless annular groove portion 22d is formed on an outer peripheral surface of the recessed portion 22 of the flow passage unit 20, and the annular groove portion 22d extends about the axis Y2. On the other hand, an endless annular protrusion portion 30b is formed on an inner peripheral surface of the nut 30, and the annular protrusion portion 30b extends about the axis Y2.

The nut 30 is made of an elastically deformable material (for example, resin material). When the nut 30 is pressed toward the annular groove portion 22d formed on the outer peripheral surface of the recessed portion 22, the annular protrusion portion 30b is engaged with the annular groove portion 22d.

In a state shown in FIG. 3 where the annular protrusion portion 30b is engaged with the annular groove portion 22d, an extremely small gap is formed between an outer peripheral surface of the annular protrusion portion 30b and an inner peripheral surface of the annular groove portion 22d. Accordingly, in a state where the nut 30 is mounted on the pressure detection unit 10, the nut 30 is rotatable with respect to the projecting portion 11 about the axis Y1. With such a configuration, an operator can rotate the nut 30 about the axis Y1 in a state where the pressure detection unit 10 is fixed to the installation surface S.

As shown in FIG. 3, the nut 30 is a circular annular member where a female thread 30a extending about the axis Y2 is formed on an inner peripheral surface of the nut 30. The nut 30 is a mechanism which allows the flow passage unit 20 to be detachably mounted on the pressure detection unit 10 by causing the female thread 30a to be fastened to a male thread 11c formed on the outer peripheral surface of the projecting portion 11 of the flow passage unit 20, or by releasing the fastening between the female thread 30a and the male thread 11c.

Next, an operation for mounting the flow passage unit 20 on the pressure detection unit 10 is described.

In mounting the flow passage unit 20 on the pressure detection unit 10 mounted on the installation surface S, an operator performs the operation with the following procedure.

First, as shown in FIG. 3, the flow passage unit 20 is disposed such that the axis Y1, which is a center axis of the pressure detection unit 10, and the axis Y2, which is a center axis of the flow passage unit 20, are made to agree with each other, and positions of the positioning protrusions 11a, 11b about the axis Y1 and positions of the positioning grooves 22b, 22c about the axis Y2 agree with each other.

FIG. 7 shows a state where the projecting portion 11 of the pressure detection unit 10 is inserted into the recessed portion 22 of the flow passage unit 20. As shown in FIG. 7, at this stage of operation, the diaphragm 12a disposed at the top portion of the projecting portion 11 and the diaphragm 22a disposed at the bottom portion of the recessed portion 22 are disposed in a spaced apart manner without coming into contact with each other.

A state shown in FIG. 7 is a state where a distal end of the female thread 30a formed on the inner peripheral surface of the nut 30 and a distal end of the male thread 11c formed on the outer peripheral surface of the pressure detection unit 10 come into contact with each other.

As described above, the distal end of the female thread 30a in the direction of the axis Y2 and the distal end of the male thread 11c in the direction of the axis Y1 come into contact with each other in a state where partial regions of the positioning protrusions 11a, 11b in the direction of the axis Y1 and partial regions of the positioning grooves 22b, 22c in the direction of the axis Y2 are engaged with each other.

Accordingly, the fastening between the female thread 30a and the male thread 11c starts in a state where positions of the inflow port 21a and the outflow port 21b of the flow passage 21 formed in the flow passage unit 20 assume predetermined positions with respect to the pressure detection unit 10.

In a state shown in FIG. 7, the female thread 30a and the male thread 11c are in contact with each other. Accordingly, even if an operator grasping the flow passage unit 20 applies a force in the direction of making the flow passage unit 20 approach the pressure detection unit 10, the flow passage unit 20 cannot be made to further approach the pressure detection unit 10.

As shown in FIG. 7, at this stage of operation, the diaphragm 12a disposed at the top portion of the projecting portion 11 and the diaphragm 22a disposed at the bottom portion of the recessed portion 22 are disposed in a spaced apart manner without coming into contact with each other.

As described above, in the pressure detection device 100 of this embodiment, even if an operator grasping the flow passage unit 20 applies a force in the direction of making the flow passage unit 20 approach the pressure detection unit 10, there is no possibility of the diaphragm 12a and the diaphragm 22a coming into contact with each other. Accordingly, it is possible to prevent the problem of the diaphragm 12a and the diaphragm 22a coming into contact with each other due to carelessness of the operator and thus being damaged.

Next, the operator rotates the nut 30 about the axis Y1 in the fastening direction (the direction indicated by "LOCK" in FIG. 1 and FIG. 2) while grasping the flow passage unit 20 in a state shown in FIG. 7. With such operations, the female thread 30a of the nut 30 and the male thread 11c of the pressure detection unit 10 are fastened to each other. By fastening the female thread 30a of the nut 30 and the male thread 11c of the pressure detection unit 10 with each other, the diaphragm 22a gradually approaches and eventually comes into contact with the diaphragm 12a. Accordingly, a state shown in FIG. 8 is brought about.

In a state shown in FIGS. 7 and 8, the positioning protrusions 11a, 11b and the positioning grooves 22b, 22c are engaged with each other. Accordingly, even if the nut 30 is rotated about the axis Y1, there is no possibility of the flow passage unit 20 rotating about the axis Y2 so that the position of the flow passage unit 20 about the axis Y2 is maintained. In this manner, the flow passage unit 20 can be mounted on the pressure detection unit 10 without causing the diaphragm 12a and the diaphragm 22a to be carelessly brought into contact with each other and without causing the flow passage unit 20 to rotate about the axis Y2.

The procedure for mounting the flow passage unit 20 which is unused on the pressure detection unit 10 has been described heretofore. A procedure for removing the flow passage unit 20 which is already used from the pressure detection unit 10 is opposite to the procedure described above.

An operator rotates the nut 30 about the axis Y1 in the fastening release direction (the direction indicated by "FREE" in FIG. 1 and FIG. 2) while grasping the flow passage unit 20 in a state shown in FIG. 8. With such operations, fastening between the female thread 30a of the nut 30 and the male thread 11c of the pressure detection unit 10 is released.

Next, the manner of operation for detecting the mounting of the flow passage unit 20 on the pressure detection unit 10 is described with reference to FIG. 9.

Figure 9:
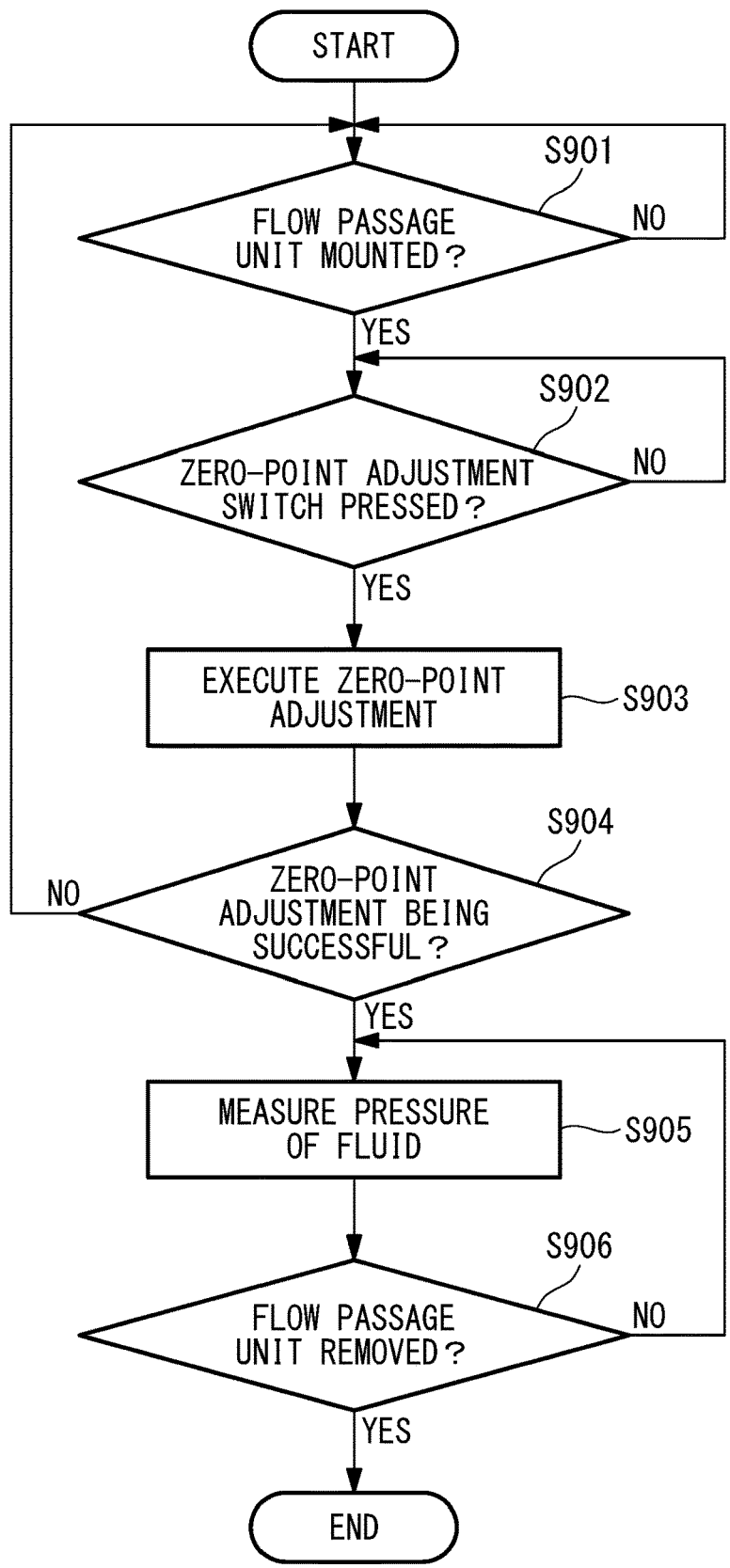
FIG. 9 is a flowchart showing processing which is executed by a sensor board of the pressure detection device of the first embodiment.

FIG. 9 is a flowchart showing processing which is executed by the sensor board 15 of the pressure detection device 100 of the first embodiment. When a CPU (not shown in the drawing) reads and executes a control program stored in a memory part (not shown in the drawing), the sensor board 15 executes processing shown in respective steps in FIG. 9.

In step S901, the sensor board 15 determines whether or not the flow passage unit 20 is mounted on the pressure detection unit 10. When the determination is YES, the processing advances to step S902. When the determination is NO, step S901 is executed again. When the sensor board 15 receives, from the mounting detection sensor 17, a mounting detection signal indicating that the flow passage unit 20 is mounted on the pressure detection unit 10, the sensor board 15 determines YES in step S901.

Figure 6:
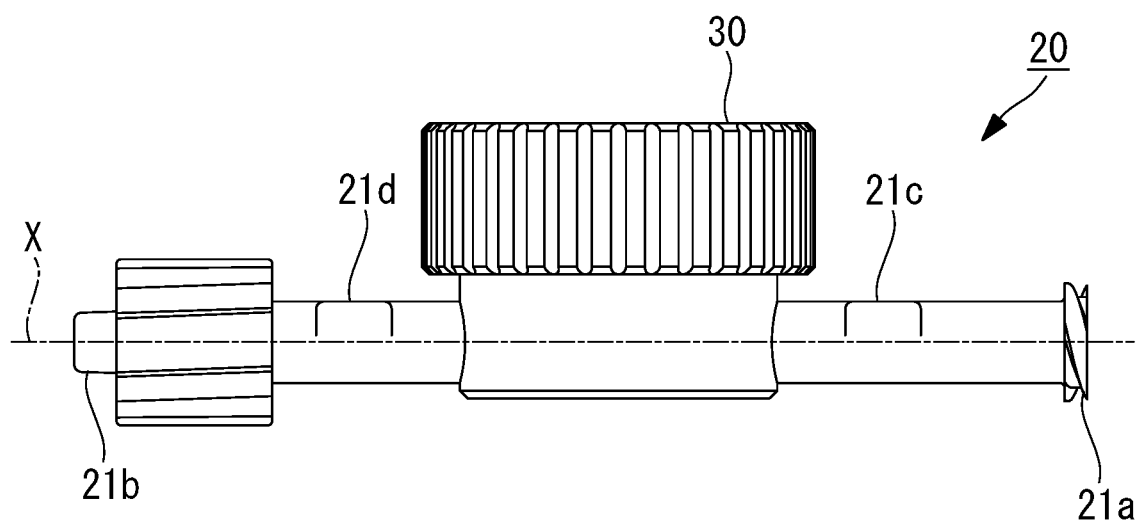
FIG. 6 is a bottom view of the flow passage unit shown in FIG. 1.

In this embodiment, as shown in FIG. 5 and FIG. 6, flat surfaces 21c, 21d are formed on the lower end of the flow passage 21 of the flow passage unit 20 at two portions which are symmetrical with respect to the axis Y2. The flat surfaces 21c, 21d are provided for reliably pressing the detecting protrusion 17a of the mounting detection sensor 17. When the detecting protrusion 17a is pressed down to a predetermined position by the flat surface 21c or the flat surface 21d, the mounting detection sensor 17 outputs a mounting detection signal to the sensor board 15.

The mounting detection sensor 17 outputs a mounting detection signal to the sensor board 15 in a state where the diaphragm 12a of the pressure detection unit 10 and the diaphragm 22a of the flow passage unit 20 are in contact with each other as shown in FIG. 8. That is, in a state where the diaphragm 12a of the pressure detection unit 10 and the diaphragm 22a of the flow passage unit 20 are in contact with each other, the mounting detection sensor 17 outputs, to the sensor board 15, a mounting detection signal indicating that the flow passage unit 20 is mounted on the pressure detection unit 10.

Further, as shown in FIG. 4, when the mounting detection sensor 17 outputs a mounting detection signal to the sensor board 15, the flow passage 21 is surrounded by the groove portions 18*a* of the guide members 18, and is guided to a predetermined mounting position where the lower end of the flow passage 21 presses down the detecting protrusion 17*a* in the downward direction. That is, the mounting detection sensor 17 detects that the flow passage unit 20 is mounted on the pressure detection unit 10 with the detection of the flow passage 21 guided to the predetermined mounting position.

In step S902, the sensor board 15 determines whether or not an operator pressed the zero-point adjustment switch 16. When the determination is YES, the processing advances to step S903. When the determination is NO, step S902 is executed again.

The sensor board 15 receives an instruction (predetermined instruction) for a zero-point adjustment which is performed by an operator so that the sensor board 15 executes a zero-point adjustment using the zero-point adjustment circuit (not shown in the drawing) in step S903. The pressure sensor 12 outputs a pressure signal at a point of time when the zero-point adjustment switch 16 is pressed, and the zero-point adjustment circuit sets the pressure signal as a reference value (zero, for example).

In step S904, the sensor board 15 determines whether or not the zero-point adjustment is successful. When the determination is YES, the processing advances to step S905. When the determination is NO, step S901 is executed again.

In this embodiment, the sensor board 15 determines YES when the difference between an upper limit value and a lower limit value of a pressure signal outputted from the pressure sensor 12 during the execution of a zero-point adjustment is less than 1% of a rated pressure value. The sensor board 15 determines NO when the difference is 1% or more of the rated output value. In this embodiment, 1% of the rated pressure value is set as a reference. However, another arbitrary value may be set as a reference.

The zero-point adjustment is successful so that, in step S905, the sensor board 15 measures a pressure of a fluid which flows through the flow passage 21 using a pressure signal set in step S903 as a reference value. To be more specific, the sensor board 15 corrects a pressure detection signal which the sensor board 15 receives from the pressure sensor 12 based on the reference value set in step S903, and the sensor board 15 outputs the pressure detection signal to a control device (not shown in the drawing) disposed outside.

In step S905, the sensor board 15 determines whether or not the flow passage unit 20 is removed from the pressure detection unit 10. When the determination is YES, processing of this flowchart is finished. When the determination is NO, step S905 is executed again. When the sensor board 15 does not receive, from the mounting detection sensor 17, a mounting detection signal indicating that the flow passage unit 20 is mounted on the pressure detection unit 10, the sensor board 15 determines YES in step S906.

As described above, the sensor board 15 of this embodiment executes a zero-point adjustment when the diaphragm 12*a* of the pressure detection unit 10 and the diaphragm 22*a* of the flow passage unit 20 are in contact with each other, and the sensor board 15 receives a mounting detection signal from the mounting detection sensor 17. That is, when the sensor board 15 does not receive a mounting detection signal from the mounting detection sensor 17, a zero-point adjustment is not executed. Accordingly, in the pressure detection device 100 of this embodiment, there is no possibility that a zero-point adjustment is executed when the flow passage unit 20 is not mounted normally on the pressure detection unit 10.

In the flowchart shown in FIG. 9, when the sensor board 15 determines that an operator pressed the zero-point adjustment switch 16 in step S902, the zero-point adjustment is executed in step S903. However, another aspect may be adopted. For example, when the sensor board 15 determines YES in step S901, the sensor board 15 may execute a zero-point adjustment in step S903 without executing step S902. In this case, the sensor board 15 performs instruction, substantially equal to instruction performed when the zero-point adjustment switch 16 is pressed, to the zero-point adjustment circuit so as to execute a zero-point adjustment. With such a configuration, a zero-point adjustment can be automatically executed corresponding to the mounting of the flow passage unit 20 on the pressure detection unit 10.

The description is made with respect to the manner of operation and advantageous effects which the above-described pressure detection device 100 of this embodiment can acquire.

According to the pressure detection device 100 of this embodiment, the flow passage unit 20 is detachably mounted on the pressure detection unit 10. Accordingly, to change a fluid which is made to flow through the flow passage 21, the flow passage unit 20 which is already used is removed from the pressure detection unit 10, and a flow passage unit 20 which is unused can be newly mounted on the pressure detection unit 10.

With such a configuration, in changing a fluid which is made to flow through the flow passage 21, it becomes unnecessary to perform a washing operation of the flow passage 21, which requires a lot of time, so that smoothness of the operation can be improved. Further, a flow passage unit 20 which is unused can be newly used and hence, safety can be improved.

According to the pressure detection device 100 of this embodiment, the mounting detection sensor 17 can detect that the flow passage unit 20 is mounted on the pressure detection unit 10 in a state where the diaphragm 12*a* and the diaphragm 22*a* are in contact with each other. Accordingly, it is possible to prevent a problem of the flow passage unit 20 being mounted on the pressure detection unit 10 in a state where the diaphragm 12*a* and the diaphragm 22*a* are not in contact with each other so that a pressure of a fluid cannot be normally detected.

As described above, according to the pressure detection device 100 of this embodiment, it is possible to improve smoothness and safety of the operation of changing a fluid which is made to flow through the flow passage 21, and it is also possible to reliably detect that the pressure detection device 100 is in a state which can normally detect a pressure of a fluid.

According to the pressure detection device 100 of this embodiment, in mounting the flow passage unit 20 on the pressure detection unit 10, the portion of the flow passage 21 on the inflow port 21*a* side and the portion of the flow passage 21 on the outflow port 21*b* side are guided to the predetermined mounting position by the pair of guide members 18. Accordingly, the flow passage unit 20 can be reliably mounted on the predetermined mounting position. Further, the mounting detection sensor 17 can reliably detect that the flow passage unit 20 is mounted normally on the pressure detection unit with the detection of the flow passage 21 guided to the predetermined mounting position.

According to the pressure detection device 100 of this embodiment, a reference value is set by the zero-point adjustment circuit in a state where the mounting detection sensor 17 detects that the flow passage unit 20 is mounted on the pressure detection unit 10. Accordingly, it is possible to prevent a problem of an incorrect pressure being erroneously set as a reference value in a state where the mounting detection sensor 17 does not detect that the flow passage unit 20 is mounted on the pressure detection unit 10.

According to the pressure detection device 100 of this embodiment, the nut 30 allows the flow passage unit 20 to be mounted on the pressure detection unit 10 in a state where the axis Y1 and the axis Y2 agree with each other, and the positions of the positioning protrusions 11*a*, 11*b* of the pressure detection unit 10 about the axis Y1 and the positions of the positioning grooves 22*b*, 22*c* of the flow passage unit 20 about the axis Y2 agree with each other. Accordingly, the direction that the flow passage unit 20 is disposed about the axis Y2 assumes a predetermined direction with respect to the direction that the pressure detection unit 10 is disposed about the axis Y1.

With such a configuration, the positions of the inflow port 21*a* and the outflow port 21*b* of the flow passage 21 formed in the flow passage unit 20 assume predetermined positions with respect to the pressure detection unit 10 so that connectivity of a pipe to be connected to the inflow port 21*a* and connectivity of a pipe to be connected to the outflow port 21*b* can be enhanced.

According to the pressure detection device 100 of this embodiment, the nut 30 allows the flow passage unit 20 to be mounted on the pressure detection unit 10 in a state where the projecting portion 11 of the pressure detection unit 10 is inserted into the recessed portion 22 of the flow passage unit 20.

With such a configuration, the diaphragm 22*a* is disposed at the bottom portion of the recessed portion 22 of the flow passage unit 20. Accordingly, in exchanging the flow passage unit 20, it is possible to suppress a problem of an operator inadvertently coming into contact with the diaphragm 22*a* and a problem of the diaphragm 22*a* coming into contact with other members thus being damaged.

According to the pressure detection device 100 of this embodiment, the diaphragm 12*a* of the pressure detection unit 10 and the diaphragm 22*a* of the flow passage unit 20 gradually approach each other when an operator rotates the nut 30 mounted on the flow passage unit 20 about the axis Y2 and, eventually, the diaphragm 12*a* and the diaphragm 22*a* come into contact with each other. With a relatively simple operation of rotating the nut 30 about the axis Y2, a distance between the diaphragm 12*a* and the diaphragm 22*a* is gradually reduced and, then, surfaces of the diaphragm 12*a* and the diaphragm 22*a* can be reliably brought into contact with each other. Accordingly, the diaphragm 12*a* and the diaphragm 22*a* can be relatively easily brought into contact with each other without causing a problem of the diaphragm 12*a* and the diaphragm 22*a* being forcefully brought into contact with each other and thus being damaged.

Second Embodiment

Next, a pressure detection device 100A according to a second embodiment of the present disclosure is described with reference to drawings.

The second embodiment is a modification of the first embodiment. Hereinafter, unless otherwise specified, the second embodiment is assumed equal to the first embodiment.

The pressure detection device 100A of the second embodiment differs from the pressure detection device of the first embodiment with respect to a point that when a mounting direction of an inflow port 21*a* and an outflow port 21*b* of a flow passage unit 20A is incorrect, a mounting detection signal, indicating that the flow passage unit 20A is mounted on a pressure detection unit 10, is not outputted.

In the pressure detection device 100 of the first embodiment, even when a mounting direction of the flow passage unit 20 on the pressure detection unit 10 is in the opposite direction with respect to the axis Y2 (in a direction which is different by 180°), a mounting detection signal is outputted which indicates that the flow passage unit 20 is mounted on the pressure detection unit 10. In this case, there is a possibility of causing a problem of a pipe expected to be connected to the inflow port 21*a* being mounted on the outflow port 21*b* or a problem of a pipe expected to be connected to the outflow port 21*b* being mounted on the inflow port 21*a*. On the other hand, in the pressure detection device 100A of the second embodiment, a recess 21*e* is provided on a lower end of a flow passage 21 of the flow passage unit 20A. Accordingly, when a mounting direction of the flow passage unit 20A on the pressure detection unit 10 is in the opposite direction with respect to the axis Y2 (in a direction which is different by 180°), a mounting detection signal is not outputted.

Figure 10:
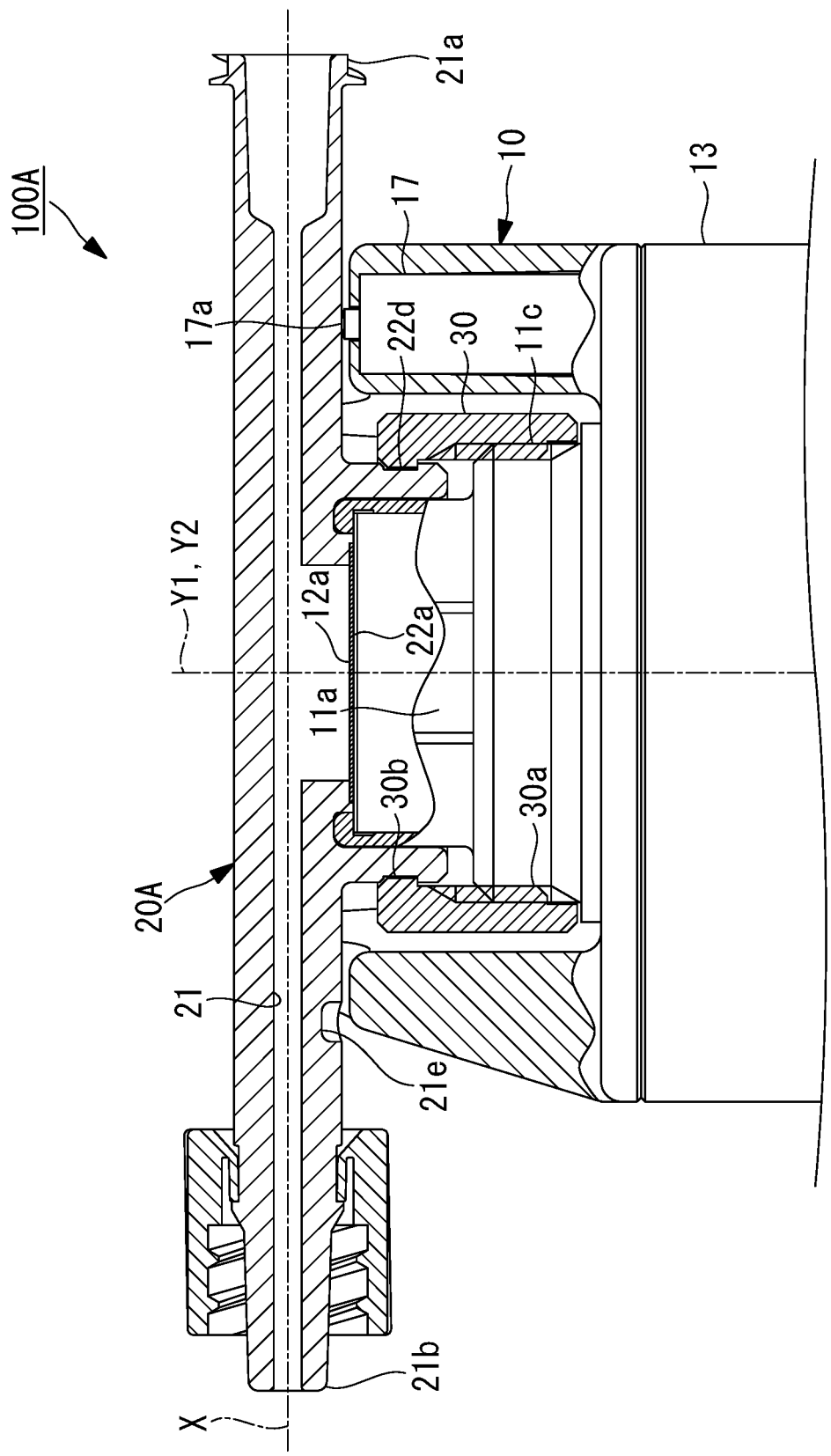
FIG. 10 is a longitudinal cross-sectional view of a pressure detection device of a second embodiment showing a state where a flow passage unit is correctly mounted on a pressure detection unit.
Figure 11:
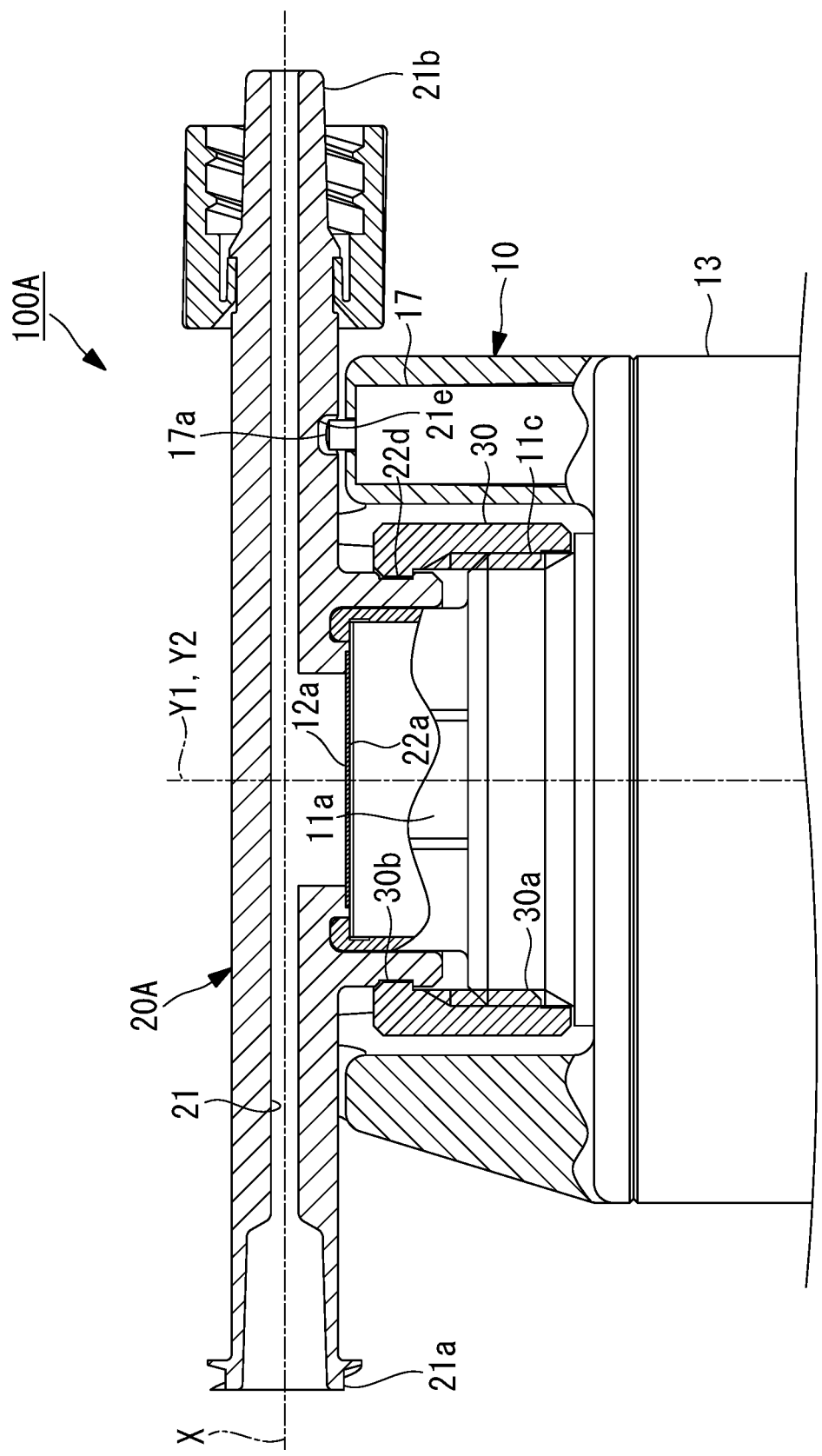
FIG. 11 is a longitudinal cross-sectional view of the pressure detection device of the second embodiment showing a state where the flow passage unit is incorrectly mounted on the pressure detection unit.

FIG. 10 is a longitudinal cross-sectional view of the pressure detection device 100A of this embodiment showing a state where the flow passage unit 20A is correctly mounted on the pressure detection unit 10. On the other hand, FIG. 11 is a longitudinal cross-sectional view of the pressure detection device 100A of this embodiment showing a state where the flow passage unit 20A is incorrectly mounted on the pressure detection unit 10.

In a state as shown in FIG. 10 where the flow passage unit 20A is correctly mounted on the pressure detection unit 10, a detecting protrusion 17*a* of a mounting detection sensor 17 is pressed down by the lower end of the flow passage 21 so that a mounting detection signal indicating that the flow passage unit 20A is mounted on the pressure detection unit 10 is outputted. On the other hand, in a state as shown in FIG. 11 where the flow passage unit 20A is incorrectly mounted on the pressure detection unit 10, a distal end of the detecting protrusion 17*a* is inserted into the recess 21*e* formed on the lower end of the flow passage 21 and hence, a mounting detection signal indicating that the flow passage unit 20A is mounted on the pressure detection unit 10 is not outputted.

As described above, according to the pressure detection device 100A of this embodiment, in a state where the flow passage unit 20A is incorrectly mounted on the pressure detection unit 10, a mounting detection signal indicating that the flow passage unit 20A is mounted on the pressure detection unit 10 is not outputted. Accordingly, it is possible to prevent a problem of a zero-point adjustment being executed in a state where the flow passage unit 20A is incorrectly mounted on the pressure detection unit 10 so that an incorrect pressure is erroneously set as a reference value.

Figure 12:
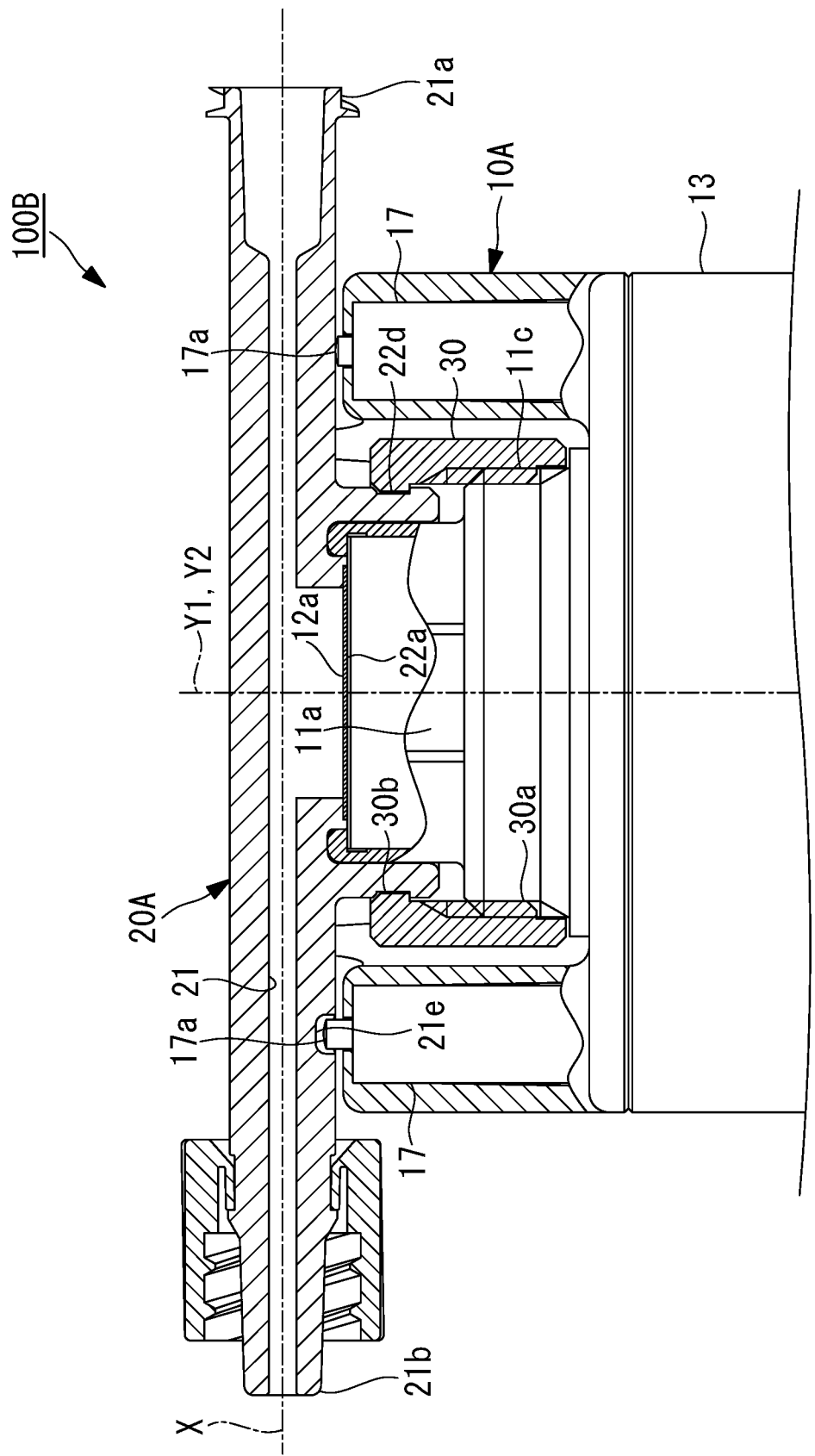
FIG. 12 is a longitudinal cross-sectional view of a pressure detection device of a modification of the second embodiment showing a state where a flow passage unit is correctly mounted on a pressure detection unit.

In the above-mentioned description, the pressure detection device 100A includes the pressure detection unit 10 which includes a single mounting detection sensor 17. However, another aspect may be adopted. For example, as shown in a modification in FIG. 12, a pressure detection device 100B may be adopted which includes a pressure detection unit 10A including a pair of mounting detection sensors 17. A sensor board 15 of the pressure detection device 100B of the modification shown in FIG. 12 determines that a flow passage unit 20A is mounted normally on the pressure detection unit 10A when a detecting protrusion 17a of the mounting detection sensor 17 disposed adjacent to an inflow port 21a is pressed, and a detecting protrusion 17a of the mounting detection sensor 17 disposed adjacent to an outflow port 21b is not pressed. On the other hand, the sensor board 15 of the pressure detection device 100B of the modification shown in FIG. 12 determines that the flow passage unit 20A is not mounted normally on the pressure detection unit 10A when the detecting protrusion 17a of the mounting detection sensor 17 disposed adjacent to the inflow port 21a is not pressed, and the detecting protrusion 17a of the mounting detection sensor 17 disposed adjacent to the outflow port 21b is pressed.

Third Embodiment

Next, a pressure detection device 100C according to a third embodiment of the present disclosure is described with reference to drawings.

The third embodiment is a modification of the first embodiment. Hereinafter, unless otherwise specified, the third embodiment is assumed equal to the first embodiment.

The pressure detection device 100C of this embodiment differs from the pressure detection device 100 of the first embodiment with respect to a point that a pair of protrusions 21f is formed on a lower end of a flow passage unit 20. Further, the pressure detection device 100C of this embodiment differs from the pressure detection device 100 of the first embodiment with respect to a point that a detecting protrusion 17a of a mounting detection sensor 17 of a pressure detection unit 10B is accommodated in a body portion 13.

Figure 13:
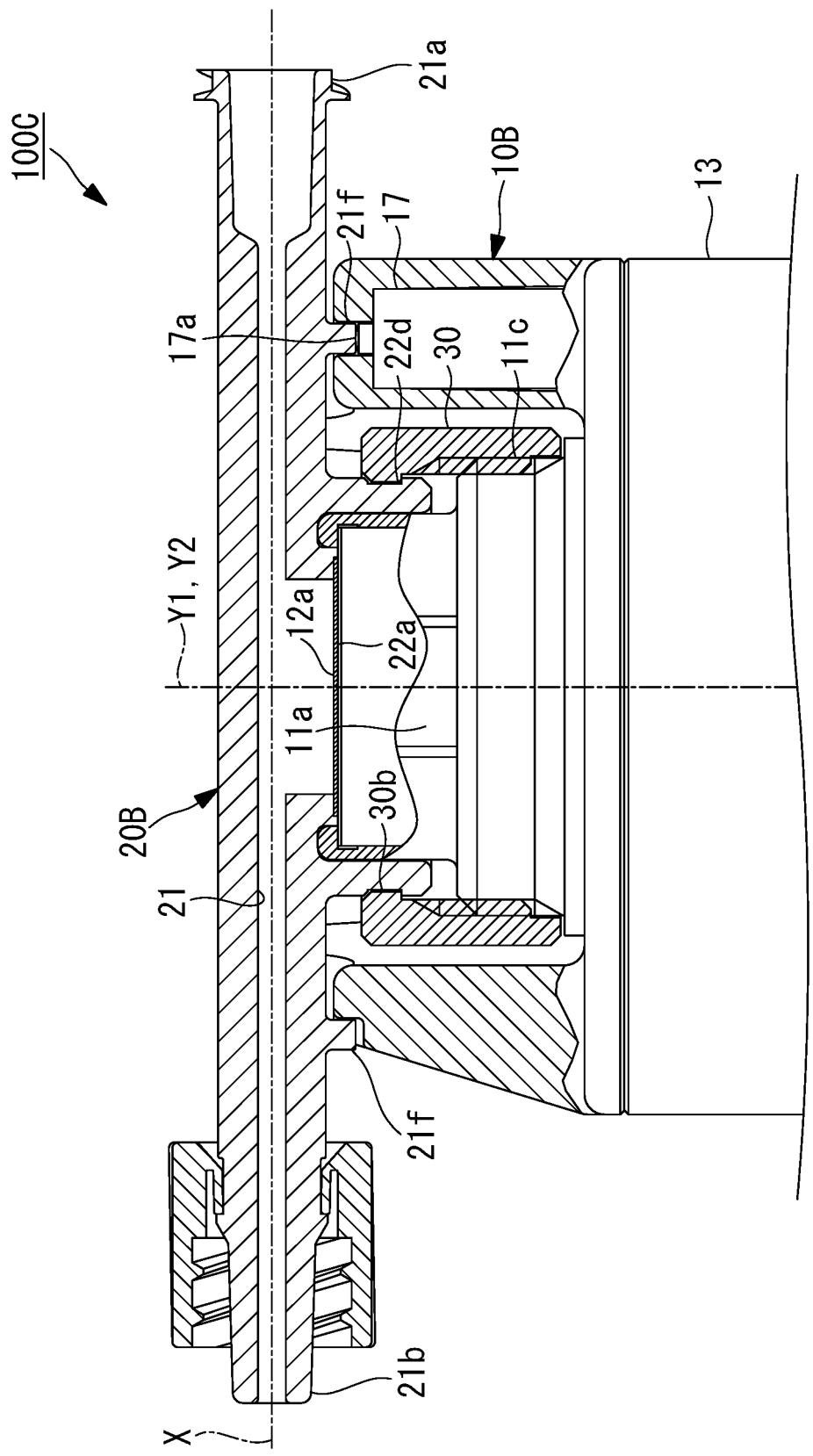
FIG. 13 is a longitudinal cross-sectional view of a pressure detection device of a third embodiment showing a state where a flow passage unit is correctly mounted on a pressure detection unit.

As shown in FIG. 13, the pressure detection device 100C of this embodiment has a structure where the protrusion 21f is inserted into the body portion 13 and presses the detecting protrusion 17a in a state where a flow passage unit 20B is correctly mounted on the pressure detection unit 10B. The detecting protrusion 17a is biased upward by a biasing member such as a spring in a state where the flow passage unit 20B is not mounted on the pressure detection unit 10B. However, a distal end of the detecting protrusion 17a is not exposed to the outside from the body portion 13. Accordingly, it is possible to prevent a problem of the detecting protrusion 17a coming into contact with other members or the like so that the mounting detection sensor 17 is damaged.

Fourth Embodiment

Next, a pressure detection device 100D according to a fourth embodiment of the present disclosure is described with reference to drawings.

The fourth embodiment is a modification of the first embodiment. Hereinafter, unless otherwise specified, the fourth embodiment is assumed equal to the first embodiment.

The pressure detection device 100 of the first embodiment includes the pressure detection unit 10 which includes a single mounting detection sensor 17. On the other hand, the pressure detection device 100D of this embodiment includes a pressure detection unit 10C which includes a pair of mounting detection sensors 17.

Figure 14:
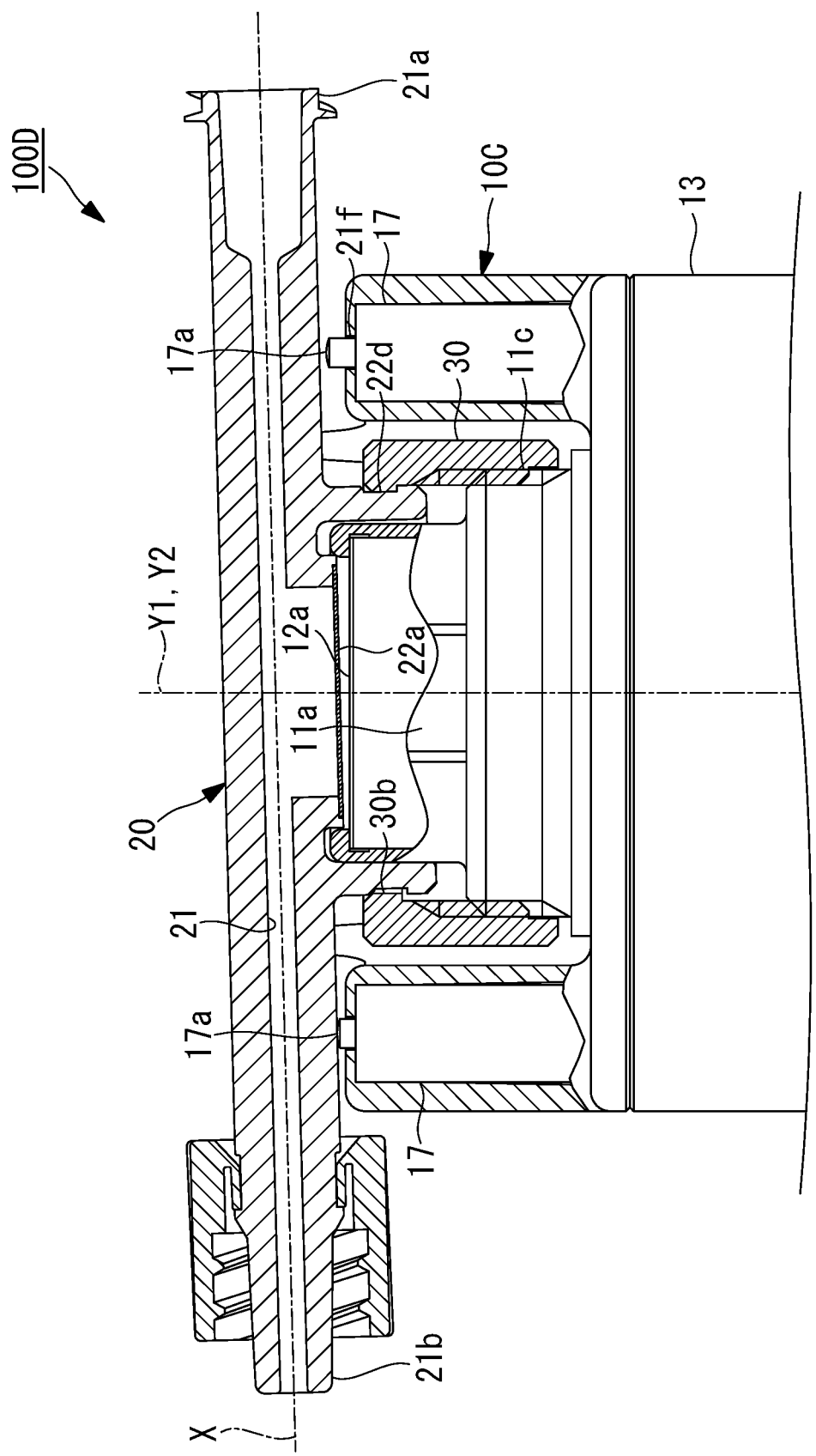
FIG. 14 is a longitudinal cross-sectional view of a pressure detection device of a fourth embodiment showing a state where a flow passage unit is incorrectly mounted on a pressure detection unit.

As shown in FIG. 14, the pressure detection device 100D of this embodiment includes the pressure detection unit 10C which includes the pair of mounting detection sensors 17. A sensor board 15 of the pressure detection unit 10C of this embodiment determines that a flow passage unit 20 is mounted normally on the pressure detection unit 10C when a detecting protrusion 17a of a mounting detection sensor 17 disposed adjacent to an inflow port 21a is pressed and when a detecting protrusion 17a of the mounting detection sensor 17 disposed adjacent to an outflow port 21b is pressed. In FIG. 14, a flow passage unit 20 is incorrectly mounted on the pressure detection unit 10C so that the detecting protrusion 17a of the mounting detection sensor 17 disposed adjacent to the inflow port 21a is not pressed. Accordingly, the sensor board 15 of this embodiment determines that the flow passage unit 20 is not mounted normally on the pressure detection unit 10C.

Fifth Embodiment

Next, a pressure detection device 100E according to a fifth embodiment of the present disclosure is described with reference to drawings.

The fifth embodiment is a modification of the first embodiment. Hereinafter, unless otherwise specified, the fifth embodiment is assumed equal to the first embodiment.

The pressure detection device 100 of the first embodiment detects that the flow passage unit 20 is mounted on the pressure detection unit 10 when the lower end of the flow passage 21 presses the detecting protrusion 17a of the mounting detection sensor 17 in the downward direction. On the other hand, the pressure detection device 100E of this embodiment detects that a flow passage unit 20 is mounted on a pressure detection unit 10E when a lower end of a nut 30 presses a detecting protrusion 17a of a mounting detection sensor 17 in the downward direction.

Figure 15:
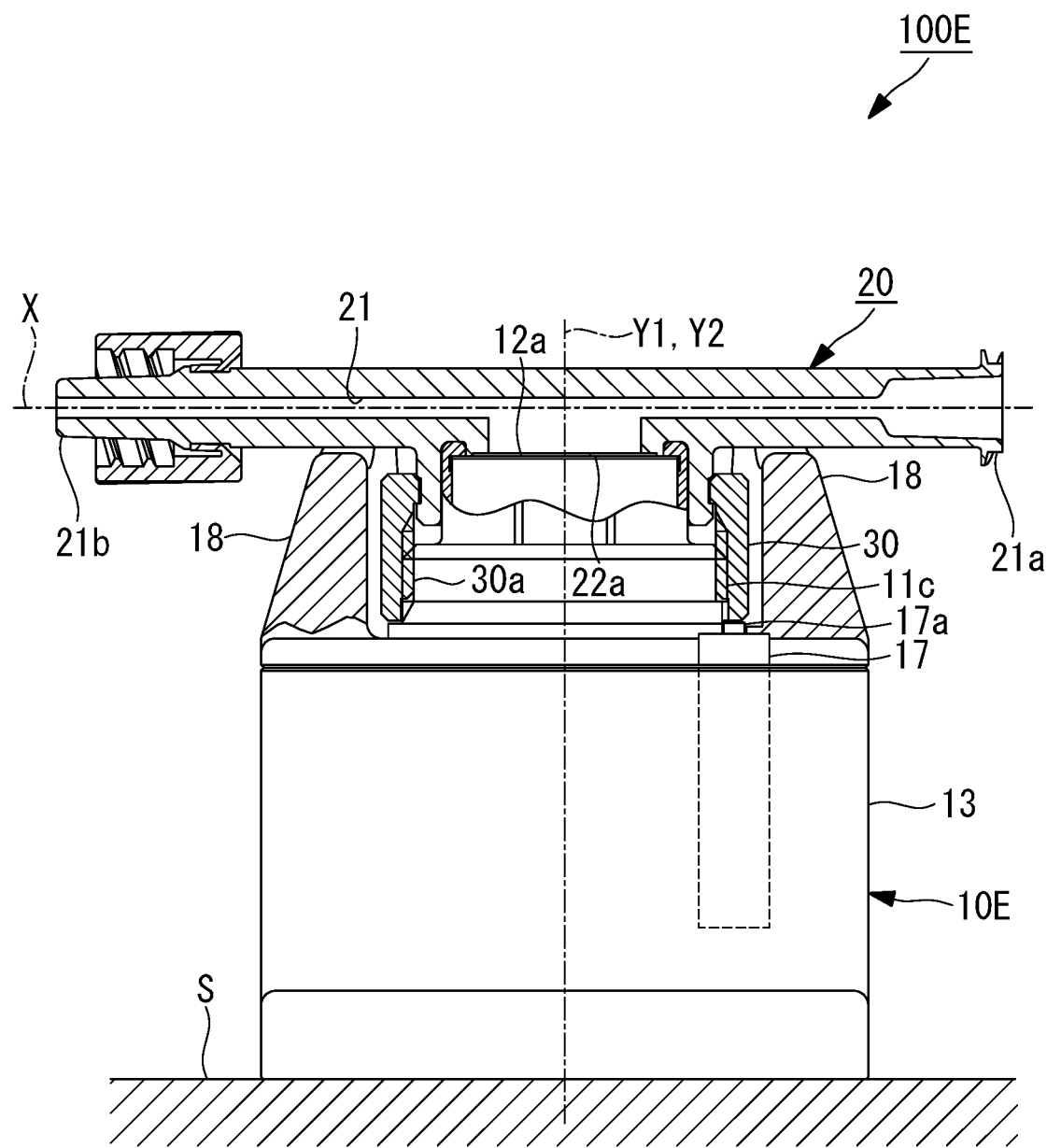
FIG. 15 is a longitudinal cross-sectional view showing a pressure detection device of a fifth embodiment.

As shown in FIG. 15, in the pressure detection device 100E of this embodiment, when a female thread 30a of the nut 30 is fastened to a male thread 11c of the pressure detection unit 10E, a lower end of the nut 30 presses down the detecting protrusion 17a in the downward direction.

According to this embodiment, when the female thread 30a of the nut 30 and the male thread 11c of the pressure detection unit 10E are reliably fastened to each other, it is possible to detect that the flow passage unit 20 is mounted on the pressure detection unit 10E.

Other Embodiments

In the description made heretofore, the positioning protrusions 11a, 11b are formed on the outer peripheral surface of the projecting portion 11 of the pressure detection unit 10, and the positioning grooves 22b, 22c are formed on the inner peripheral surface of the recessed portion 22 of the flow passage unit 20. However, another aspect may be adopted.

For example, positioning grooves may be formed on the outer peripheral surface of the projecting portion 11 of the pressure detection unit 10, and positioning protrusions may be formed on the inner peripheral surface of the recessed portion 22 of the flow passage unit 20. That is, the positioning protrusions may be formed in place of the above-described positioning grooves, and the positioning grooves may be formed in place of the positioning protrusions.

In the above-mentioned description, the mounting detection sensor 17 is a sensor which outputs a mounting detection signal when the detecting protrusion 17a is pressed in the downward direction. However, another aspect may be adopted.

For example, the mounting detection sensor may be formed of a transmission-type photo sensor where a light emitting element and a light receiving element are disposed so as to face each other, and a mounting detection signal is outputted when an element intervenes between the light emitting element and the light receiving element. In this case, an obstructing element (not shown in the drawing) is provided on the lower end of the flow passage 21 of the flow passage unit 20, and the obstructing element intervenes between the light emitting element and the light receiving element when the flow passage unit 20 is mounted normally on the pressure detection unit 10.

The invention claimed is:

1. A pressure detection device comprising:
a pressure detection unit configured to detect a pressure transmitted to a pressure detection surface;
a flow passage unit in which a flow passage and a pressure transmitting surface are formed, a fluid being made to flow through the flow passage along a flow direction from an inflow port to an outflow port, the pressure transmitting surface being configured to transmit a pressure of the fluid flowing through the flow passage to the pressure detection surface; and
a mounting mechanism configured to allow the flow passage unit to be detachably mounted on the pressure detection unit, wherein:
the pressure detection unit includes a detection part configured to detect that the flow passage unit is mounted on the pressure detection unit in a state where the pressure detection surface and the pressure transmitting surface are in contact with each other.

2. The pressure detection device according to claim 1, wherein:
the pressure detection unit includes a pair of guide parts having groove portions configured to guide a portion of the flow passage on an inflow port side and a portion of the flow passage on an outflow port side to a predetermined mounting position in mounting the flow passage unit on the pressure detection unit; and
the detection part is disposed on at least either one of the pair of guide parts, and the detection part detects that the flow passage unit is mounted on the pressure detection unit with the detection of the flow passage guided to the predetermined mounting position.

3. The pressure detection device according to claim 1, wherein:
the pressure detection unit includes a setting part configured to set a pressure detected by the pressure detection surface as a reference value corresponding to a predetermined instruction; and
the setting part sets the reference value corresponding to the predetermined instruction in a state where the detection part detects that the flow passage unit is mounted on the pressure detection unit.

4. The pressure detection device according to claim 1, wherein:
the pressure detection unit includes a first positioning portion extending in a first axial direction extending along a first axis orthogonal to the pressure detection surface;
the flow passage unit includes a second positioning portion extending in a second axial direction extending along a second axis orthogonal to the pressure transmitting surface; and
the mounting mechanism allows the flow passage unit to be mounted on the pressure detection unit in a state where the first axis and the second axis agree with each other, and a position of the first positioning portion about the first axis and a position of the second positioning portion about the second axis agree with each other.

5. The pressure detection device according to claim 4, wherein:
the pressure detection unit has a projecting portion where the pressure detection surface is disposed at a top portion of the projecting portion, and the first positioning portion is formed on an outer peripheral surface of the projecting portion;
the flow passage unit has a recessed portion where the pressure transmitting surface is disposed at a bottom portion of the recessed portion, and the second positioning portion is formed on an inner peripheral surface of the recessed portion; and
the mounting mechanism allows the flow passage unit to be mounted on the pressure detection unit in a state where the projecting portion of the pressure detection unit is inserted into the recessed portion of the flow passage unit.

6. The pressure detection device according to claim 5, wherein:
the first positioning portion is formed of a plurality of protrusions formed on the outer peripheral surface of the projecting portion;
the second positioning portion is formed of a plurality of grooves formed on the inner peripheral surface of the recessed portion; and
the mounting mechanism allows the flow passage unit to be mounted on the pressure detection unit in a state where the first axis and the second axis agree with each other, and respective positions of the plurality of protrusions about the first axis and respective positions of the plurality of grooves about the second axis agree with each other.

7. The pressure detection device according to claim 5, wherein:
the mounting mechanism is formed of a nut mounted on the flow passage unit in a rotatable manner about the second axis, a female thread being formed on an inner peripheral surface of the nut;
a male thread is formed on an outer peripheral surface of the pressure detection unit disposed more outward than the projecting portion; and
the pressure transmitting surface comes into contact with the pressure detection surface by fastening the female thread formed on the nut to the male thread.

8. The pressure detection device according to claim 7, wherein:
a distal end of the female thread in a direction of the first axis and a distal end of the male thread in a direction of the second axis come into contact with each other in a state where a portion of the first positioning portion in the direction of the first axis and a portion of the second positioning portion in the direction of the second axis are engaged with each other.

* * * * *